US009078868B2

(12) United States Patent
Murakami et al.

(10) Patent No.: US 9,078,868 B2
(45) Date of Patent: Jul. 14, 2015

(54) THERAPEUTIC AGENT FOR ACCELERATING RECOVERY OF ANIMAL UNDER MEDICAL TREATMENT

(75) Inventors: Noboru Murakami, Miyazaki (JP); Keiko Nakahara, Miyazaki (JP); Kenji Kangawa, Suita (JP); Yujiro Hayashi, Kobe (JP)

(73) Assignees: UNIVERSITY OF MIYAZAKI, Miyazaki-shi, Miyazaki (JP); NATIONAL CEREBRAL AND CARDIOVASCULAR CENTER, Suita-shi, Osaka (JP); DAIICHI SANKYO COMPANY, LIMITED, Tokyo (JP)

( * ) Notice: Subject to any disclaimer, the term of this patent is extended or adjusted under 35 U.S.C. 154(b) by 142 days.

(21) Appl. No.: 13/522,203

(22) PCT Filed: Jan. 14, 2011

(86) PCT No.: PCT/JP2011/050579
§ 371 (c)(1),
(2), (4) Date: Sep. 7, 2012

(87) PCT Pub. No.: WO2011/087102
PCT Pub. Date: Jul. 21, 2011

(65) Prior Publication Data
US 2013/0005654 A1   Jan. 3, 2013

(30) Foreign Application Priority Data
Jan. 15, 2010  (JP) .................... 2010-006557

(51) Int. Cl.
*A61K 38/25* (2006.01)
*A61K 38/00* (2006.01)
*A61K 38/22* (2006.01)

(52) U.S. Cl.
CPC ............... *A61K 38/25* (2013.01); *A61K 38/00* (2013.01); *A61K 38/2264* (2013.01)

(58) Field of Classification Search
CPC ............... A61K 38/2264; A61K 38/00
See application file for complete search history.

(56) References Cited

U.S. PATENT DOCUMENTS

| 7,385,026 B1 | 6/2008 | Kangawa et al. |
| 2005/0009744 A1 | 1/2005 | Isaksson et al. |
| 2006/0217296 A1 | 9/2006 | Jansson |
| 2007/0037751 A1 | 2/2007 | Lange et al. |
| 2008/0269116 A1 | 10/2008 | Taub et al. |
| 2010/0093604 A1 | 4/2010 | Leonard et al. |

FOREIGN PATENT DOCUMENTS

| JP | 2004-277402 | 10/2004 |
| JP | 2005-507949 | 3/2005 |
| JP | 2005-289863 | 10/2005 |
| JP | 2006-241098 | 9/2006 |
| JP | 2007-523048 | 8/2007 |
| JP | 2007-537276 | 12/2007 |
| JP | 2008-127377 | 6/2008 |
| JP | 2008-237377 | 10/2008 |
| JP | 2009-51847 | 3/2009 |
| WO | 01/07475 | 2/2001 |
| WO | 02/060472 | 8/2002 |
| WO | 2004/014412 | 2/2004 |
| WO | 2008/136511 | 11/2008 |
| WO | 2009/119792 | 10/2009 |

OTHER PUBLICATIONS

Exhaustion definition downloaded from http://medical-dictionary.thefreedictionary.com/p/exhaustion[Aug. 19, 2014 4:02:55 PM].*
Supplementary European Search Report dated Jul. 31, 2013 issued in EP 11 73 2972.
K. Shah et al., "Human Ghrelin Ameliorates Organ Injury and Improves Survival after Radiation Injury Combined with Severe Sepsis," Molecular Medicine (Baltimore), vol. 15, Nos. 11-12, Nov. 2009, pp. 407-414.
M. Yukawa et al., "Peripheral ghrelin treatment stabilizes body weights of senescent male Brown Norway rats at baseline and after surgery," American Journal of Physiology—Regulatory Integrative and Comparative Physiology, vol. 294, No. 5, May 2008, pp. R1453-R1460.
T. Akamizu et al., "Effects of ghrelin treatment on patients undergoing total hip replacement for osteoarthritis: Different outcomes from studies in patients with cardiac and pulmonary cachexia," Journal of the American Geriatrics Society, vol. 56, No. 12, Dec. 2008, pp. 2363-2365. International Search Report mailed Mar. 15, 2011 in PCT/JP2011/050579 filed Jan. 14, 2011.
International Preliminary Report on Patentability mailed May 22, 2012 in PCT/JP2011/050579 filed Jan. 14, 2011.
Óscar Álvarez-Garcia et al., "Administration of ghrelin to young uraemic rats increases food intake transiently, stimulates growth hormone secretion and does not improve longitudinal growth", Nephrology Dialysis Transplantation, Feb. 22, 2007, pp. 1309-1313, vol. 22.
Rocco Barazzoni et al., "Combined effects of ghrelin and higher food intake enhance skeletal muscle mitochondrial oxidative capacity and AKT phosphorylation in rats with chronic kidney disease", Kidney International, 2010, pp. 23-28, vol. 77.

(Continued)

*Primary Examiner* — Daniel C Gamett
(74) *Attorney, Agent, or Firm* — Drinker Biddle & Reath

(57) ABSTRACT

An object of the present invention is to provide a therapeutic agent for accelerating recovery to accelerate a return to normal physical conditions by administering to an animal not in good health and under medical treatment, a treatment method, and the like. There is provided a therapeutic agent for accelerating recovery for animal use to accelerate the improvement of a physical condition of an animal under medical treatment which has a decreased activity (vigor) and is exhausted, which contains ghrelin or a derivative thereof or a pharmaceutically acceptable salt thereof as an active ingredient and improves one or more of evaluation parameters consisting of activity (vigor), blood cell test values, biochemical test values, body temperature, the degree of anger or anxiety, and respiratory rate.

25 Claims, No Drawings

(56) References Cited

OTHER PUBLICATIONS

Mark D. Deboer et al., "Ghrelin Treatment of Chronic Kidney Disease: Improvements in Lean Body Mass and Cytokine Profile", Endocrinology, 2008, pp. 827-835, vol. 149.
Elena Gonzalez-Rey et al., "Therapeutic Action of Ghrelin in a Mouse Model of Colitis", Gastroenterology, 2006, pp. 1707-1720, vol. 130.
Hiroshi Hosoda et al., "Biological, Physiological, and Pharmacological Aspects of Ghrelin", Journal of Pharmacological Sciences, 2006, pp. 398-410, vol. 100.
Andrew Howard et al., "A Receptor in Pituitary and Hypothalamus That Functions in Growth Hormone Release", Science, 1996, pp. 974-977, vol. 273.
Kazutomo Imahori et al., Dictionary of Biological Chemistry, The third edition, Tokyo Kagaku Doujin Co., Ltd, Oct. 8, 1998, pp. 1060 (partial translation).
Masayasu Kojima et al., "Ghrelin is a growth-hormone-releasing acylated peptide from stomach", Nature, Dec. 9, 1999, pp. 656-660, vol. 402.
Márta Korbonits et al., "Ghrelin-a hormone with multiple functions", Frontiers in Neuroendocrinology, 2004, pp. 27-68, vol. 25.
Aart J. Van Der Lely et al., "Biological, Physiological, Pathophysiological, and Pharmacological Aspects of Ghrelin", Endocrine Reviews, 2004, pp. 426-557, vol. 25(3).
Michael Lutter et al., "The orexigenic hormone ghrelin defends against depressive symptoms of chronic stress", Nature Neuroscience, 2008, pp. 752-753, vol. 11.
Noritoshi Nagaya et al., "Effects of Ghrelin Administration on Left Ventricular Function, Exercise Capacity, and Muscle Wasting in Patients with Chronic Heart Failure", Circulation, 2004, pp. 3674-3679, vol. 110.
Noritoshi Nagaya et al., "Treatment of Cachexia with Ghrelin in Patients with COPD", CHEST, 2005, pp. 1187-1193, vol. 128.
Masamitsu Nakazato et al., "A role for ghrelin in the central regulation of feeding", Nature, 2001, pp. 194-198, vol. 409.
Nicola M. Neary et al., "Ghrelin Increases Energy Intake in Cancer Patients with Impaired Appetite: Acute, Randomized, Placebo-Controlled Trial", The Journal of Clinical Endocrinology & Metabolism, 2004, pp. 2832-2836, vol. 89.
John A. Rudd et al., "Anti-emetic activity of ghrelin in ferrets exposed to the cytotoxic anti-cancer agent cisplatin", Neuroscience Letters, 2006, pp. 79-83, vol. 392.
Mitsuyo Shintani et al., "Ghrelin, an Endogenous Growth Hormone Secretagogue, Is a Novel Orexigenic Peptide That Antagonizes Leptin Action through the Activation of Hypothalamic Neuropeptide Y/Y1 Receptor Pathway", Diabetes, 2001, pp. 227-232, vol. 50.
Ryo Takeda et al., "Ghrelin Improves Renal Function in Mice with Ischemic Acute Renal Failure", Journal of the American Society of Nephrology, 2006, pp. 113-121, vol. 17.
Matthias Tschöp et al., "Ghrelin induces adiposity in rodents", Nature, 2000, pp. 908-913, vol. 407.
A.M. Wren et al., "The Novel Hypothalamic Peptide Ghrelin Stimulates Food Intake and Growth Hormone", Endocrinology, 2000, pp. 4325-4328, vol. 141, No. 11.
Wikipedia page of "Chronic kidney disease," available at http://en.wikipedia.org/w/index.php?title=Chronic_kidney_disease&redirect=no (last visited Dec. 5, 2014).
Google Translation of "Let Tsukiao well with disease 'About chronic kidney disease' Part 3," available at http://www.anicom-page.com/labo/2013/05/post-469.html (last visited Dec. 5, 2014).
Yokoyarna, et al., "Influencing the between-feeding and endocrine responses of plasma ghrelin in healthy dogs", European Journal of Endocrinology (2005) 152 155-160.
Ariga, et al,, "Endogenous acyl ghrelin is involved in mediating spontaneous phase III-like contractions of the rat stomach", Neurogastroenterol Motil (2007) 19, 675-680.
Masuda, et al., "Ghrelin Stimulates Gastric Acid Secretion and Motility in Rats", Biochemical and Biophysical Research Communications 276, 905-908 (2000).
Ohno, et al., "Ghrelin does not stimulate gastrointestinal motility and gastric emptying: an experimental study of conscious dogs", Neurogastroenterol Motil (2006) 18, 129-135.

* cited by examiner

SEQUENCE LISTING

<160> NUMBER OF SEQ ID NOS: 23

<210> SEQ ID NO 1
<211> LENGTH: 28
<212> TYPE: PRT
<213> ORGANISM: Canis familiaris

<400> SEQUENCE: 1

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Canis familiaris

<400> SEQUENCE: 2

Gly Ser Ser Phe Leu Ser Pro Glu His Gln Lys Leu Gln Arg Lys Glu
1               5                   10                  15

Ser Lys Lys Pro Pro Ala Lys Leu Gln Pro Arg
            20                  25

<210> SEQ ID NO 3
<211> LENGTH: 27
<212> TYPE: PRT
<213> ORGANISM: Felis silvestris catus

<400> SEQUENCE: 3

Gly Ser Ser Phe Leu Ser Pro Glu His Gln Lys Val Gln Arg Lys Glu
1               5                   10                  15

Ser Lys Lys Pro Pro Ala Lys Leu Gln Pro Arg
            20                  25

<210> SEQ ID NO 4
<211> LENGTH: 28
<212> TYPE: PRT
<213> ORGANISM: Rattus norvegicus

<400> SEQUENCE: 4

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 5
<211> LENGTH: 27
<212> TYPE: PRT
<213> ORGANISM: Rattus norvegicus

<400> SEQUENCE: 5

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 6
<211> LENGTH: 28
<212> TYPE: PRT
<213> ORGANISM: Mus musculus

<400> SEQUENCE: 6

```
Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25
```

<210> SEQ ID NO 7
<211> LENGTH: 28
<212> TYPE: PRT
<213> ORGANISM: Sus scrofa

<400> SEQUENCE: 7

```
Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25
```

<210> SEQ ID NO 8
<211> LENGTH: 27
<212> TYPE: PRT
<213> ORGANISM: Bos taurus

<400> SEQUENCE: 8

```
Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25
```

<210> SEQ ID NO 9
<211> LENGTH: 27
<212> TYPE: PRT
<213> ORGANISM: Ovis aries

<400> SEQUENCE: 9

```
Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25
```

<210> SEQ ID NO 10
<211> LENGTH: 28
<212> TYPE: PRT
<213> ORGANISM: Equus caballus

<400> SEQUENCE: 10

```
Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25
```

<210> SEQ ID NO 11
<211> LENGTH: 24
<212> TYPE: PRT
<213> ORGANISM: Gallus domesticus

<400> SEQUENCE: 11

```
Gly Ser Ser Phe Leu Ser Pro Thr Tyr Lys Asn Ile Gln Gln Gln Lys
1               5                   10                  15

Gly Thr Arg Lys Pro Thr Ala Arg
            20
```

<210> SEQ ID NO 12

```
<211> LENGTH: 24
<212> TYPE: PRT
<213> ORGANISM: Gallus domesticus

<400> SEQUENCE: 12

Gly Ser Ser Phe Leu Ser Pro Thr Tyr Lys Asn Ile Gln Gln Gln Lys
1               5                   10                  15

Asp Thr Arg Lys Pro Thr Ala Arg
            20

<210> SEQ ID NO 13
<211> LENGTH: 26
<212> TYPE: PRT
<213> ORGANISM: Gallus domesticus

<400> SEQUENCE: 13

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
            20                  25

<210> SEQ ID NO 14
<211> LENGTH: 28
<212> TYPE: PRT
<213> ORGANISM: Homo sapiens

<400> SEQUENCE: 14

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 15
<211> LENGTH: 27
<212> TYPE: PRT
<213> ORGANISM: Homo sapiens

<400> SEQUENCE: 15

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 16
<211> LENGTH: 28
<212> TYPE: PRT
<213> ORGANISM: Macaca mulatta

<400> SEQUENCE: 16

Gly Ser Ser Phe Leu Ser Pro Glu His Gln Arg Ala Gln Gln Arg Lys
1               5                   10                  15

Glu Ser Lys Lys Pro Pro Ala Lys Leu Gln Pro Arg
            20                  25

<210> SEQ ID NO 17
<211> LENGTH: 27
<212> TYPE: PRT
<213> ORGANISM: Cervidae

<400> SEQUENCE: 17

Gly Ser Ser Phe Leu Ser Pro Glu His Gln Lys Leu Gln Arg Lys Glu
1               5                   10                  15
```

```
Pro Lys Lys Pro Ser Gly Arg Leu Lys Pro Arg
            20                  25
```

<210> SEQ ID NO 18
<211> LENGTH: 27
<212> TYPE: PRT
<213> ORGANISM: Cervidae

<400> SEQUENCE: 18

```
Gly Ser Ser Phe Leu Ser Pro Asp His Gln Lys Leu Gln Arg Lys Glu
1               5                   10                  15

Pro Lys Lys Pro Ser Gly Arg Leu Lys Pro Arg
            20                  25
```

<210> SEQ ID NO 19
<211> LENGTH: 27
<212> TYPE: PRT
<213> ORGANISM: Capra aegagrus hircus

<400> SEQUENCE: 19

```
Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25
```

<210> SEQ ID NO 20
<211> LENGTH: 28
<212> TYPE: PRT
<213> ORGANISM: Oryctolagus cuniculus

<400> SEQUENCE: 20

```
Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25
```

<210> SEQ ID NO 21
<211> LENGTH: 28
<212> TYPE: PRT
<213> ORGANISM: Meleagris gallopavo

<400> SEQUENCE: 21

```
Gly Ser Ser Phe Leu Ser Pro Ala Tyr Lys Asn Ile Gln Gln Gln Lys
1               5                   10                  15

Asp Thr Arg Lys Pro Thr Ala Arg Leu His Pro Arg
            20                  25
```

<210> SEQ ID NO 22
<211> LENGTH: 28
<212> TYPE: PRT
<213> ORGANISM: Anser sp.

<400> SEQUENCE: 22

```
Gly Ser Ser Phe Leu Ser Pro Glu Phe Lys Lys Ile Gln Gln Gln Asn
1               5                   10                  15

Asp Pro Thr Lys Thr Thr Ala Lys Ile His Arg Arg
            20                  25
```

<210> SEQ ID NO 23
<211> LENGTH: 28
<212> TYPE: PRT
<213> ORGANISM: Coturnix japonica

```
<400> SEQUENCE: 23

Gly Ser Ser Phe Leu Ser Pro Ala Tyr Lys Asn Ile Gln Gln Lys
1               5                   10                  15

Asn Thr Arg Lys Pro Ala Ala Arg Leu His Arg Arg
            20                  25
```

THERAPEUTIC AGENT FOR ACCELERATING RECOVERY OF ANIMAL UNDER MEDICAL TREATMENT

CROSS REFERENCE TO RELATED APPLICATIONS

This application is a National Stage of International Application No. PCT/JP2011/050579, filed Jan. 14, 2011, and which claims benefit of Japanese Patent Application No.: 2010-006557 filed Jan. 15, 2010, both of which are incorporated by reference herein.

REFERENCE TO A SEQUENCE LISTING

A Sequence Listing containing SEQ ID NOS: 1-23 is incorporated herein by reference.

TECHNICAL FIELD

The present invention relates to a therapeutic agent for accelerating the recovery of an animal not in good health. Specifically, the present invention relates to a therapeutic agent for accelerating recovery to improve a physical condition of an animal not in good health and thereby restore the animal early, which contains ghrelin or a derivative thereof as an active ingredient, a method for treatment by administering the substance, and the like.

BACKGROUND ART

Improving the conditions of animals not in good health which require medical treatment and thereby allowing the animals to return to their owners early is important for the animals and the owners as well as veterinarians and veterinary hospitals. Early recovery is desired particularly for animals hospitalized for medical treatment, such as a surgery. Favorable courses and stabilized pathological conditions, which accelerate the recovery of the hospitalized animals, are expected to contribute to the improvement of quality of life (QOL) of animals and owners and the reduction of burdens on veterinarians and veterinary hospitals.

Ghrelin is a hormone discovered in the stomach in 1999 and has an amino acid sequence consisting of 28 residues with a very rare chemical structure in which the amino acid at the 3rd position from the N terminus of the sequence is acylated with a fatty acid (Non Patent Literature 1 and Patent Literature 1). Ghrelin is an endogenous brain-gut hormone that acts on the growth hormone secretagogue-receptor 1a (GHS-R1a) (Non Patent Literature 2) and increases growth hormone (GH) secretion from the pituitary gland.

Ghrelin was first isolated from rats and purified as an endogenous GHS-R ligand for the GHS-R1a. Then, ghrelins having a similar primary structure were isolated from vertebrates other than rats, such as humans, mice, porcines, chickens, bovines, equines, ovines, canines, and felines, and amino acid sequences thereof are known (Patent Literature 1). Examples of ghrelins derived from animals are listed below.

```
Canine:
                                    (SEQ ID NO: 1)
GSS (n-octanoyl) FLSPEHQKLQQRKESKKPPAKLQPR (SEQ ID NO: 2)
GSS (n-octanoyl) FLSPEHQKLQRKESKKPPAKLQPR
```

-continued

```
Feline:
                                    (SEQ ID NO: 3)
GSS (n-octanoyl) FLSPEHQKVQRKESKKPPAKLQPR Rat:
                                    (SEQ ID NO: 4)
GSS (n-octanoyl) FLSPEHQKAQQRKESKKPPAKLQPR (SEQ ID NO: 5)
GSS (n-octanoyl) FLSPEHQKAQRKESKKPPAKLQPR Mouse:
                                    (SEQ ID NO: 6)
GSS (n-octanoyl) FLSPEHQKAQQRKESKKPPAKLQPR Porcine:
                                    (SEQ ID NO: 7)
GSS (n-octanoyl) FLSPEHQKVQQRKESKKPAAKLKPR Bovine:
                                    (SEQ ID NO: 8)
GSS (n-octanoyl) FLSPEHQKLQRKEAKKPSGRLKPR Ovine:
                                    (SEQ ID NO: 9)
GSS (n-octanoyl) FLSPEHQKLQRKEPKKPSGRLKPR Equine:
                                   (SEQ ID NO: 10)
GSS (n-butanoyl) FLSPEHHKVQHRKESKKPPAKLKPR Chicken:
                                   (SEQ ID NO: 11)
GSS (n-octanoyl) FLSPTYKNIQQQKGTRKPTAR (SEQ ID NO: 12)
GSS (n-octanoyl) FLSPTYKNIQQQKDTRKPTAR (SEQ ID NO: 13)
GSS (n-octanoyl) FLSPTYKNIQQQKDTRKPTARLH Human:
                                   (SEQ ID NO: 14)
GSS (n-octanoyl) FLSPEHQRVQQRKESKKPPAKLQPR (SEQ ID NO: 15)
GSS (n-octanoyl) FLSPEHQRVQ-RKESKKPPAKLQPR Monkey:
                                   (SEQ ID NO: 16)
GSS (n-octanoyl) FLSPEHQRAQQRKESKKPPAKLQPR Dear:
                                   (SEQ ID NO: 17)
GSS (n-octanoyl) FLSPEHQKLQ-RKEPKKPSGRLKPR (SEQ ID NO: 18)
GSS (n-octanoyl) FLSPDHQKLQ-RKEPKKPSGRLKPR Goat:
                                   (SEQ ID NO: 19)
GSS (n-octanoyl) FLSPEHQKLQ-RKEPKKPSGRLKPR Rabbit:
                                   (SEQ ID NO: 20)
GSS (n-octanoyl) FLSPEHQKVQQRKESKKPAAKLKPR Wild turkey:
                                   (SEQ ID NO: 21)
GSS (n-octanoyl) FLSPAYKNIQQQKDTRKPTARLHPR Goose:
                                   (SEQ ID NO: 22)
GSS (n-octanoyl) FLSPEFKKIQQQNDPTKTTAKIHPR Japanese quail:
                                   (SEQ ID NO: 23)
GSS (n-octanoyl) FLSPAYKNIQQQKNTRKPAARLHRR
```

(Amino acid residues are expressed in the single letter code in the above list.)

The peptides listed above are peptides that have a specific structure in which a side chain hydroxyl group of the serine residue (S) at the 3rd position is acylated with a fatty acid, such as butanoic acid, octanoic acid, or decanoic acid. Other than ghrelin, no bioactive peptide having such a hydrophobic modification structure has been isolated from living organisms.

In addition to the peptide compounds listed above, examples of substances that act on the GHS-R1a include the GHRP-2, which is a peptide compound, and MK-0677, which is a low molecular weight compound (Non Patent Literature 4).

Recent studies have revealed that ghrelin increases appetite, that subcutaneous administration of ghrelin increases body weight and body fat (Non Patent Literatures 3 to 6), and that ghrelin has effects of improving cardiac function and the like (Non Patent Literatures 7 to 9). Furthermore, ghrelin has a GH secretagogue action and an appetite increasing action. Through the increased appetite, ghrelin is therefore expected to further effectively exhibit an action of burning fat and converting the fat into energy through a GH action and an effect of building muscle through an expressed anabolic action of GH (Non Patent Literature 9).

A more effective therapeutic agent for accelerating recovery is demanded to treat animals not in good health which require medical treatment, particularly to restore animals hospitalized for a surgery or the like early.

CITATION LIST

Patent Literature

Patent Literature 1: International Publication No. WO 01/07475

Non Patent Literature

Non Patent Literature 1: Kojima et al.: Nature, 402, pp. 656-660 (1999)
Non Patent Literature 2: Howard et al.: Science, 273, pp. 974-977 (1996)
Non Patent Literature 3: Wren et al.: Endocrinology, 141, pp. 4325-4328 (2000)
Non Patent Literature 4: Nakazato et al.: Nature, 409, pp. 194-198 (2001)
Non Patent Literature 5: Shintani et al.: Diabetes, 50, pp. 227-232 (2001)
Non Patent Literature 6: Tshop et al.: Nature, 407, pp. 908-913 (2000)
Non Patent Literature 7: Lely et al.: Endocr. Rev., 25, pp. 656-660 (2004)
Non Patent Literature 8: Korbonits et al.: Front. Neuroendocrinol., 25, pp. 27-68 (2004)
Non Patent Literature 9: Kangawa et al.: J. Pharmacol. Sci., 100, pp. 398-410 (2006)

SUMMARY OF INVENTION

Technical Problem

An object of the present invention is to provide a therapeutic agent for accelerating recovery for accelerating a return of physical conditions to normal in an animal not in good health and under medical treatment by administering the agent to the animal, a method for treatment, and the like.

Solution to Problem

The inventors of the present invention found that administration of ghrelin to animals not in good health because of various pathological conditions, particularly to animals hospitalized for treatment, improved various parameters indicating animal conditions (for example, one or more of activity (vigor), blood cell test values, biochemical test values, body temperature, the degree of anger or anxiety, and respiratory rate), and that administration of ghrelin could accelerate the early recovery of animals under medical treatment. Furthermore, the inventors of the present invention found that physical conditions of animals which were unable to move because of worsened pathological conditions were also improved after administration of ghrelin in terms of these parameters.

Specifically, the present invention relates to a therapeutic agent for accelerating recovery for animal use to accelerate the improvement of physical or psychological conditions in animals under medical treatment, which contains ghrelin or a derivative thereof or a pharmaceutically acceptable salt thereof as an active ingredient.

Furthermore, the present invention is relates to a method for treatment to accelerate the improvement of physical conditions in animals under medical treatment, comprising administration of ghrelin or a derivative thereof or a pharmaceutically acceptable salt thereof.

Furthermore, the present invention relates to use of ghrelin or a derivative thereof or a pharmaceutically acceptable salt thereof for production of a therapeutic agent for accelerating recovery for animal use to accelerate the improvement of physical conditions in animals under medical treatment.

From the above, the present invention relates specifically to the following.

(1) A therapeutic agent for accelerating recovery for animal use to accelerate the improvement of physical conditions in an animal under medical treatment which has a decreased activity (vigor) and is exhausted, which contains ghrelin or a derivative thereof or a pharmaceutically acceptable salt thereof as an active ingredient and improves one or more of evaluation parameters consisting of activity (vigor), blood cell test values, biochemical test values, body temperature, the degree of anger or anxiety, and respiratory rate.

(2) The therapeutic agent for accelerating recovery according to the above (1), wherein the animal is an animal after surgery.

(3) The therapeutic agent for accelerating recovery according to the above (1) or (2), wherein the blood cell in the blood cell test values is white blood cell, platelet, or hemoglobin.

(4) The therapeutic agent for accelerating recovery according to any one of the above (1) to (3), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), serum potassium (K), or C-reactive protein (CRP).

(5) The therapeutic agent for accelerating recovery according to any one of the above (1) to (4), wherein the animal is an animal which has a disease selected from a genital disease, a tumor, an urological disease, a bone disease, an infection, a parasitism, an inflammatory disease, and a gastrointestinal tract disease.

(6) The therapeutic agent for accelerating recovery according to any one of the above (1) to (5), wherein the animal is an animal under medical treatment for a disease selected from lower urological syndrome, chronic renal failure, renal failure, urinary retention, urethroplasty, cystolithiasis, infectious respiratory syndrome, heart failure, osteoarthritis, luxation, bone resorption, chronic hepatitis, cystitis, malnutrition, hypoglycemia, debility, jaundice, circulatory insufficiency, multiple organ failure, pulmonary edema, pneumonia, anemia, tabefaction, diarrhea, vomiting, wheezing, feline acquired immunodeficiency syndrome (FIV), feline leukemia virus (FELV) infection, feline viral rhinotracheitis (FVR), canine parvovirus (CPV) infection, pyrexia, a liver disease, mite infestation, filariasis, hemobartonellosis, babesiosis, habu bite, anaphylaxis, a falling accident, a traffic accident, trauma, laceration, bite, rib fracture, pelvic fracture, femoral fracture, other fractures, limb amputation, disc hernia, diaphragmatic hernia, pneumothorax, skin seborrhea, peritonitis, heat stroke, acute enteritis, ileus, intussusception, gastric volvulus, and burn.

(7) The therapeutic agent for accelerating recovery according to any one of the above (1) to (6), wherein a combination of a reason for medical treatment and an evaluation parameter is selected from the following:

1) the reason for the medical treatment is a genital disease, such as pyometra or surgical removal of a reproductive organ, and the evaluation parameter is one or more of BUN and CRP, which are biochemical test values, body temperature, and activity (vigor);

2) the reason for the medical treatment is a tumor, such as mammary gland tumor, ovarian cyst, testicle tumor, salivary gland cyst, or liver tumor mass, and the evaluation parameter is one or more of activity (vigor), body temperature, and the degree of anger or anxiety;

3) the reason for the medical treatment is an orthopedic disease, such as a fracture, an accident, luxation, or disc hernia, and the evaluation parameter is one or more of body temperature, the degree of anger or anxiety, respiratory rate, activity (vigor), and GOT, GPT, BUN, and CPK, which are biochemical test values;

4) the reason for the medical treatment is a renal dysfunction, such as urinary retention, cystolithiasis, or renal failure, and the evaluation parameter is one or more of white blood cell count and platelet count, which are blood cell test values, creatinine (Cre), which is a biochemical test value, and activity (vigor);

5) the reason for the medical treatment is an infection or a parasitism, and the evaluation parameter is one or more of BUN, which is a biochemical test value, respiratory rate, and activity (vigor);

6) the reason for the medical treatment is an inflammatory disease, such as dermatitis, bite, or laceration, and the evaluation parameter is one or more of body temperature, activity (vigor), and GOT, GPT, and BUN, which are biochemical test values; and 7) the reason for the medical treatment is a digestive system disease, such as vomiting, diarrhea, malnutrition, debility, ileus, or intussusception, and the evaluation parameter is activity (vigor).

(8) The therapeutic agent for accelerating recovery according to any one of the above (1) to (7), wherein the ghrelin or a derivative thereof or a pharmaceutically acceptable salt thereof is a peptide, or a pharmaceutically acceptable salt thereof, selected from the group consisting of (i) a peptide that has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide that has an amino acid sequence including deletion, substitution, and/or addition of one to several amino acids in an amino acid sequence between the amino acid residue at the 5th position from the amino terminus and the carboxy terminus of any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.

The ghrelin or a derivative thereof or a pharmaceutically acceptable salt thereof used in the present invention may be a peptide containing the above-mentioned amino acid sequences. Specifically, other amino acids may be added to the N terminus.

(9) The therapeutic agent for accelerating recovery according to the above (8), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.

(10) The therapeutic agent for accelerating recovery according to the above (9), wherein the ghrelin is a peptide that has an amino acid sequence of SEQ ID NO: 1 in which the side chain hydroxyl group of the serine residue at the 3rd position from the amino terminus is acylated with an n-octanoyl group.

(11) The therapeutic agent for accelerating recovery according to any one of the above (1) to (10), which contains 0.001 to 100 mg per dose unit of ghrelin or a derivative thereof or a pharmaceutically acceptable salt thereof as an active ingredient.

(12) A treatment method for accelerating the improvement of a physical condition in an animal under medical treatment which has a decreased activity (vigor) and is exhausted, comprising administration of ghrelin or a derivative thereof or a pharmaceutically acceptable salt thereof to the animal under medical treatment to improve one or more of evaluation parameters consisting of activity (vigor), blood cell test values, biochemical test values, body temperature, the degree of anger or anxiety, and respiratory rate of the animal.

(13) The treatment method according to the above (12), wherein the animal is an animal after surgery.

(14) The treatment method according to the above (12) or (13), wherein the blood cell in the blood cell test values is white blood cell, platelet, or hemoglobin.

(15) The treatment method according to any one of the above (12) to (14), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), serum potassium (K), or C-reactive protein (CRP).

(16) The treatment method according to any one of the above (12) to (15), wherein the animal is an animal which has a disease selected from a genital disease, a tumor, a urological disease, a bone disease, an infection, a parasitism, an inflammatory disease, and a gastrointestinal tract disease.

(17) The treatment method according to any one of the above (12) to (15), wherein the animal is an animal under medical treatment for a disease selected from lower urological syndrome, chronic renal failure, renal failure, urinary retention, urethroplasty, cystolithiasis, infectious respiratory syndrome, heart failure, osteoarthritis, luxation, bone resorption, chronic hepatitis, cystitis, malnutrition, hypoglycemia, debility, jaundice, circulatory insufficiency, multiple organ failure, pulmonary edema, pneumonia, anemia, tabefaction, diarrhea, vomiting, wheezing, feline acquired immunodeficiency syndrome (FIV), feline leukemia virus (FELV) infection, feline viral rhinotracheitis (FVR), canine parvovirus (CPV) infection, pyrexia, a liver disease, mite infestation, filariasis, hemobartonellosis, babesiosis, habu bite, anaphylaxis, a falling accident, a traffic accident, trauma, laceration, bite, rib fracture, pelvic fracture, femoral fracture, other fractures, limb amputation, disc hernia, diaphragmatic hernia, pneumothorax, skin seborrhea, peritonitis, heat stroke, acute enteritis, ileus, intussusception, gastric volvulus, and burn.

(18) The treatment method according to any one of the above (12) to (17), wherein a combination of a reason for medical treatment and an evaluation parameter is selected from the following:

1) the reason for the medical treatment is a genital disease, such as pyometra or surgical removal of a reproductive organ, and the evaluation parameter is one or more of BUN and CRP, which are biochemical test values, body temperature, and activity (vigor);

2) the reason for the medical treatment is a tumor, such as mammary gland tumor, ovarian cyst, testicle tumor, salivary gland cyst, or liver tumor mass, and the evaluation parameter is one or more of body temperature, the degree of anger or anxiety, and activity (vigor);

3) the reason for the medical treatment is an orthopedic disease, such as a fracture, an accident, luxation, or disc hernia, and the evaluation parameter is one or more of body temperature, the degree of anger or anxiety, respiratory rate, activity (vigor), and GOT, GPT, BUN, and CPK, which are biochemical test values;

4) the reason for the medical treatment is a renal dysfunction, such as urinary retention, cystolithiasis, or renal failure, and the evaluation parameter is one or more of white blood cell count and platelet count, which are blood cell test values, Cre, which is a biochemical test value, and activity (vigor);

5) the reason for the medical treatment is an infection or a parasitism, and the evaluation parameter is one or more of BUN, which is a biochemical test value, respiratory rate, and activity (vigor);

6) the reason for the medical treatment is an inflammatory disease, such as dermatitis, bite, or laceration, and the evaluation parameter is one or more of body temperature, activity (vigor), and GOT, GPT, and BUN, which are biochemical test values; and 7) the reason for the medical treatment is a digestive system disease, such as vomiting, diarrhea, malnutrition, debility, ileus, or intussusception, and the evaluation parameter is activity (vigor).

(19) The treatment method according to any one of the above (12) to (18), wherein the ghrelin or a derivative thereof or a pharmaceutically acceptable salt thereof is a peptide, or a pharmaceutically acceptable salt thereof, selected from the group consisting of (i) a peptide that has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide that has an amino acid sequence including deletion, substitution, and/or addition of one to several amino acids in an amino acid sequence between the amino acid residue at the 5th position from the amino terminus and the carboxy terminus of any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.

(20) The treatment method according to the above (19), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.

(21) The treatment method according to the above (20), wherein the ghrelin is a peptide that has an amino acid sequence of SEQ ID NO: 1 in which the side chain hydroxyl group of the serine residue at the 3rd position from the amino terminus is acylated with an n-octanoyl group.

(22) The treatment method according to anyone of the above (12) to (21), comprising administration of a dose of 0.001 to 100 mg of ghrelin or a derivative thereof or a pharmaceutically acceptable salt thereof as an active ingredient.

(23) Use of ghrelin or a derivative thereof or a pharmaceutically acceptable salt thereof for production of a therapeutic agent for accelerating recovery for animal use to accelerate the improvement of physical conditions in an animal under medical treatment which has a decreased activity (vigor) and is exhausted, which improves one or more of evaluation parameters consisting of activity (vigor), blood cell test values, biochemical test values, body temperature, the degree of anger or anxiety, and respiratory rate.

(24) The use according to the above (23), wherein the animal is an animal after surgery.

(25) The use according to the above (23) or (24), wherein the blood cell of the blood cell test values is white blood cell, platelet, or hemoglobin.

(26) The use according to any one of the above (23) to (25), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), serum potassium (K), or C-reactive protein (CRP).

(27) The use according to any one of the above (23) to (26), wherein the animal is an animal which has a disease selected from a genital disease, a tumor, a urological disease, a bone disease, an infection, a parasitism, an inflammatory disease, and a gastrointestinal tract disease.

(28) The use according to any one of the above (23) to (27), wherein the animal is an animal under medical treatment for a disease selected from lower urological syndrome, chronic renal failure, renal failure, urinary retention, urethroplasty, cystolithiasis, infectious respiratory syndrome, heart failure, osteoarthritis, luxation, bone resorption, chronic hepatitis, cystitis, malnutrition, hypoglycemia, debility, jaundice, circulatory insufficiency, multiple organ failure, pulmonary edema, pneumonia, anemia, tabefaction, diarrhea, vomiting, wheezing, feline acquired immunodeficiency syndrome (FIV), feline leukemia virus (FELV) infection, feline viral rhinotracheitis (FVR), canine parvovirus (CPV) infection, pyrexia, a liver disease, mite infestation, filariasis, hemobartonellosis, babesiosis, habu bite, anaphylaxis, a falling accident, a traffic accident, trauma, laceration, bite, rib fracture, pelvic fracture, femoral fracture, other fractures, limb amputation, disc hernia, diaphragmatic hernia, pneumothorax, skin seborrhea, peritonitis, heat stroke, acute enteritis, ileus, intussusception, gastric volvulus, and burn.

(29) The use according to any one of the above (23) to (28), wherein a combination of a reason for medical treatment and an evaluation parameter is selected from the following:

1) the reason for the medical treatment is a genital disease, such as pyometra or surgical removal of a reproductive organ, and the evaluation parameter is one or more of BUN and CRP, which are biochemical test values, body temperature, and activity (vigor);

2) the reason for the medical treatment is a tumor, such as mammary gland tumor, ovarian cyst, testicle tumor, salivary gland cyst, or liver tumor mass, and the evaluation parameter is one or more of body temperature, the degree of anger or anxiety, and activity (vigor);
3) the reason for the medical treatment is an orthopedic disease, such as a fracture, luxation, disc hernia, or an accident, and the evaluation parameter is one or more of body temperature, the degree of anger or anxiety, respiratory rate, activity (vigor), and GOT, GPT, BUN, and CPK, which are biochemical test values;
4) the reason for the medical treatment is a renal dysfunction, such as urinary retention, cystolithiasis, or renal failure, and the evaluation parameter is one or more of white blood cell count and platelet count, which are blood cell test values, Cre, which is a biochemical test value, and activity (vigor);
5) the reason for the medical treatment is an infection or a parasitism, and the evaluation parameter is one or more of BUN, which is a biochemical test value, respiratory rate, and activity (vigor);
6) the reason for the medical treatment is an inflammatory disease, such as dermatitis, bite, or laceration, and the evaluation parameter is one or more of body temperature, activity (vigor), and GOT, GPT, and BUN, which are biochemical test values; and
7) the reason for the medical treatment is a digestive system disease, such as vomiting, diarrhea, malnutrition, debility, ileus, or intussusception, and the evaluation parameter is activity (vigor).
(30) The use according to any one of the above (23) to (29), wherein the ghrelin or a derivative thereof or a pharmaceutically acceptable salt thereof is a peptide, or a pharmaceutically acceptable salt thereof, selected from the group consisting of (i) a peptide that has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide that has an amino acid sequence including deletion, substitution, and/or addition of one to several amino acids in an amino acid sequence between the amino acid residue at the 5th position from the amino terminus and the carboxy terminus of any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.
(31) The use according to the above (30), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.
(32) The use according to the above (31), wherein the ghrelin is a peptide that has an amino acid sequence of SEQ ID NO: 1 in which the side chain hydroxyl group of the serine residue at the 3rd position from the amino terminus is acylated with an n-octanoyl group.
(33) The use according to any one of the above (23) to (32), wherein the therapeutic agent for accelerating recovery for animal use contains 0.001 to 100 mg per dose unit of ghrelin or a derivative thereof or a pharmaceutically acceptable salt thereof as an active ingredient.
(34) Ghrelin or a derivative thereof or a pharmaceutically acceptable salt thereof for use to accelerate the improvement of physical condition in an animal under medical treatment which has a decreased activity (vigor) and is exhausted, which improves one or more of evaluation parameters consisting of activity (vigor), blood cell test values, biochemical test values, body temperature, the degree of anger or anxiety, and respiratory rate.
(35) The ghrelin or a derivative thereof or a pharmaceutically acceptable salt thereof according to the above (34), wherein the animal is an animal after surgery.
(36) The ghrelin or a derivative thereof or a pharmaceutically acceptable salt thereof according to the above (34) or (35), wherein the blood cell of the blood cell test values is white blood cell, platelet, or hemoglobin.
(37) The ghrelin or a derivative thereof or a pharmaceutically acceptable salt thereof according to any one of the above (34) to (36), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), serum potassium (K), or C-reactive protein (CRP).
(38) The ghrelin or a derivative thereof or a pharmaceutically acceptable salt thereof according to any one of the above (34) to (37), wherein the animal is an animal which has a disease selected from a genital disease, a tumor, a urological disease, a bone disease, an infection, a parasitism, an inflammatory disease, and a gastrointestinal tract disease.
(39) The ghrelin or a derivative thereof or a pharmaceutically acceptable salt thereof according to any one of the above (34) to (38), wherein the animal is an animal under medical treatment for a disease selected from lower urological syndrome, chronic renal failure, renal failure, urinary retention, urethroplasty, cystolithiasis, infectious respiratory syndrome, heart failure, osteoarthritis, luxation, bone resorption, chronic hepatitis, cystitis, malnutrition, hypoglycemia, debility, jaundice, circulatory insufficiency, multiple organ failure, pulmonary edema, pneumonia, anemia, tabefaction, diarrhea, vomiting, wheezing, feline acquired immunodeficiency syndrome (FIV), feline leukemia virus (FELV) infection, feline viral rhinotracheitis (FVR), canine parvovirus (CPV) infection, pyrexia, a liver disease, mite infestation, filariasis, hemobartonellosis, babesiosis, habu bite, anaphylaxis, a falling accident, a traffic accident, trauma, laceration, bite, rib fracture, pelvic fracture, femoral fracture, other fractures, limb amputation, disc hernia, diaphragmatic hernia, pneumothorax, skin seborrhea, peritonitis, heat stroke, acute enteritis, ileus, intussusception, gastric volvulus, and burn.
(40) The ghrelin or a derivative thereof or a pharmaceutically acceptable salt thereof according to any one of the above (34) to (39), wherein a combination of a reason for medical treatment and an evaluation parameter is selected from the following:
1) the reason for the medical treatment is a genital disease, such as pyometra or surgical removal of a reproductive organ, and the evaluation parameter is one or more of BUN and CRP, which are biochemical test values, body temperature, and activity (vigor);
2) the reason for the medical treatment is a tumor, such as mammary gland tumor, ovarian cyst, testicle tumor, salivary gland cyst, or liver tumor mass, and the evaluation parameter is one or more of body temperature, the degree of anger or anxiety, and activity (vigor);
3) the reason for the medical treatment is an orthopedic disease, such as a fracture, luxation, disc hernia, or an accident, and the evaluation parameter is one or more of body temperature, the degree of anger or anxiety, respiratory rate, activity (vigor), and GOT, GPT, BUN, and CPK, which are biochemical test values;

4) the reason for the medical treatment is a renal dysfunction, such as urinary retention, cystolithiasis, or renal failure, and the evaluation parameter is one or more of white blood cell count and platelet count, which are blood cell test values, Cre, which is a biochemical test value, and activity (vigor);
5) the reason for the medical treatment is an infection or a parasitism, and the evaluation parameter is one or more of BUN, which is a biochemical test value, respiratory rate, and activity (vigor);
6) the reason for the medical treatment is an inflammatory disease, such as dermatitis, bite, or laceration, and the evaluation parameter is one or more of body temperature, activity (vigor) and GOT, GPT, and BUN, which are biochemical test values; and
7) the reason for the medical treatment is a digestive system disease, such as vomiting, diarrhea, malnutrition, debility, ileus, or intussusception, and the evaluation parameter is activity (vigor).
(41) The ghrelin or a derivative thereof or a pharmaceutically acceptable salt thereof according to any one of the above (34) to (40), wherein the ghrelin or a derivative thereof or a pharmaceutically acceptable salt thereof is a peptide, or a pharmaceutically acceptable salt thereof, selected from the group consisting of (i) a peptide that has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide that has an amino acid sequence including deletion, substitution, and/or addition of one to several amino acids in an amino acid sequence between the amino acid residue at the 5th position from the amino terminus and the carboxy terminus of any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.
(42) The ghrelin or a derivative thereof or a pharmaceutically acceptable salt thereof according to the above (41), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.
(43) The ghrelin or a derivative thereof or a pharmaceutically acceptable salt thereof according to the above (42), wherein the ghrelin is a peptide that has an amino acid sequence of SEQ ID NO: 1 in which the side chain hydroxyl group of the serine residue at the 3rd position from the amino terminus is acylated with an n-octanoyl group.
(44) The ghrelin or a derivative thereof or a pharmaceutically acceptable salt thereof according to any one of the above (34) to (43), wherein the therapeutic agent for accelerating recovery for animal use contains 0.001 to 100 mg per dose unit of ghrelin or a derivative thereof or a pharmaceutically acceptable salt thereof as an active ingredient.

An evaluation parameter may be used solely, or two or more evaluation parameters may be used in combination. Preferred examples of the combination include vigor and biochemical test values, vigor and blood cell test values, and vigor, biochemical test values and blood cell test values.

A dose unit refers to a dose per one administration. Administration can be performed once to several times daily.

Advantageous Effects of Invention

The present invention has revealed that ghrelin or a derivative thereof or a pharmaceutically acceptable salt thereof has an action of accelerating a return to normal physical conditions, in animals with various pathological conditions. Based on this effect, a return to normal physical conditions can be accelerated by administering ghrelin or a derivative thereof or a pharmaceutically acceptable salt thereof to animals with poor physical conditions resulting from a pathological condition or a surgery. Because of this effect, the present invention can provide a therapeutic agent for accelerating recovery and a treatment method that are effective for the treatment of an animal not in good health which requires medical treatment, particularly for early recovery of an animal which has undergone a surgery.

DESCRIPTION OF EMBODIMENTS

Target animals of the agent of the present invention are not limited as long as the animals are useful animals. For example, the animals may be any one of humans, mammals other than humans, birds, and ornamental animals. Animals with a disease or after surgery are preferred. Preferred examples are animals which have lost vigor because of a disease or a surgery and are in a physically or psychologically difficult condition such as, for example, being bedridden or being unable to get up or to walk. Specific examples of such animal species include human, canine, feline, mouse, rat, rabbit, bovine, equine, porcine, and monkey. Canine and feline are particularly preferred.

The present invention is implemented to the advantage of animals after surgery. Examples of the surgery include contraception, castration, surgical removal of a suppurative lesion, and surgery for a genital disease (pyometra, etc.), a tumor disease (mammary gland tumor, etc.), an orthopedic disease (disc hernia, injury by a traffic accident, etc.), a urological disease (urethral opening formation, etc.), a bone disease (fracture, etc.) and a gastrointestinal tract disease. For example, when the therapeutic agent of the present invention is used in an animal after surgery, a surprisingly remarkable effect is exhibited. Furthermore, the therapeutic agent of the present invention has a marked effect on animals with poor physical conditions due to a disease (renal dysfunction, such as chronic renal failure, etc.) which do not undergo a surgery.

The target animal of the therapeutic agent of the present invention is "an animal under medical treatment which has a decreased activity (vigor) and is exhausted". The expression "animal under medical treatment which has a decreased activity (vigor) and is exhausted" means, for example, an animal which has lost strength and vigor and is exhausted because of a chronic disease, such as renal failure, a tumor, an infection, an accident, a surgery, or the like. Specific examples of a state of activity (vigor) are: 1. lifeless (the animal is unable to move and is exhausted), 2. slightly responsive to an external stimulus (the animal is slightly responsive to the movement of a health care professional, follows with the eyes, lifts the head, and tries to get up), 3. capable of moving in response to an external stimulus (the animal is able to get up and move in the cage although slowly), 4. as usual with normal movement, 5. more active than normal, 6. considerably more active than normal, and 7. very much more active than normal. Preferred examples of the target animal include animals after surgery for the treatment of a disease selected from a genital disease, a tumor, a urological disease, a bone disease, disc hernia, and a gastrointestinal tract disease. The bone diseases also include fractures. Furthermore, preferred examples of the target animal also include animals under medical treatment for a disease selected from lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, feline acquired immunodeficiency syndrome (FIV), feline leukemia virus (FELV) infection, canine parvovirus (CPV) infection, feline viral rhinotracheitis (FVR), a liver disease, filariasis, hemobartonellosis, babesiosis, habu bite, anaphylaxis, a falling accident, rib fracture, and burn. The therapeutic agent of the present invention is preferably used to accelerate the improvement of physical conditions in animals under such medical treatment. Furthermore, the therapeutic agent of the present invention may be used in combination with a therapeutic agent of a specific disease. In the present invention, the term "physical conditions" may include a specific "psychological condition" (for example, being calm or restless) and may be referred to as "physical or psychological conditions".

Ghrelin was administered to animals not in good health which required medical treatment because of various pathological conditions (in particular, animals which underwent a surgery for treatment), and various parameters indicating physical conditions in animals were then analyzed. As specifically described later in the Examples, specific parameters (activity [vigor], hematology parameters [blood cell test values], serum biochemistry parameters [biochemical test values], body temperature, the degree of anger or anxiety, and respiratory rate) were found to be improved. Therefore, administration of the substance to animals requiring medical treatment can improve physical conditions of the animals early and accelerate recovery. Ghrelin is very useful particularly because ghrelin can improve physical conditions and accelerate the recovery of canines and felines, which are often brought into veterinary hospitals as animals requiring medical treatment. The term "improvement" preferably means that values of evaluation parameters reach the range between improvement by approximately 20% or more from physical conditions before administration of the agent of the present invention as a lower limit and improvement by 100%, i.e., returning to normal values, as an upper limit.

Furthermore, improvement in activity (vigor) and the degree of anger or anxiety means that scores or the like corresponding to the evaluation criteria described below or the like are improved after administration of ghrelin (for example, a score or the like for vigor is increased, and a score or the like for the degree of anger or anxiety is decreased).

Such an action of accelerating the improvement of physical conditions in animals requiring medical treatment can be exhibited through a growth hormone secretagogue receptor. Specifically, when animals requiring medical treatment owing to various pathological conditions or accidents lose vigor and have abnormal blood cell test values or biochemical test values, high body temperature, or the like, ghrelin or a derivative thereof or a pharmaceutically acceptable salt thereof, which is a substance according to the present invention that acts on a growth hormone secretagogue receptor, can be used as an active ingredient of a therapeutic agent for accelerating recovery to improve physical conditions in the animals early and accelerate recovery during the treatment. Furthermore, ghrelin or a derivative thereof or a pharmaceutically acceptable salt thereof can be used during the treatment to improve physical conditions in animals requiring medical treatment and restore the animals early. Ghrelin or a derivative thereof or a pharmaceutically acceptable salt thereof can also be used to produce a therapeutic agent for accelerating recovery to improve physical conditions in animals requiring medical treatment and restore the animals early. Ghrelin or a derivative thereof or a pharmaceutically acceptable salt thereof can be used to accelerate the improvement of physical conditions in animals under medical treatment by improving one or more of evaluation parameters consisting of activity (vigor), blood cell test values, biochemical test values, body temperature, the degree of anger or anxiety, and respiratory rate in animals under medical treatment.

The above-mentioned parameters can be investigated by known techniques. For example, as described later in the Examples, a test substance is intravenously, subcutaneously, intramuscularly, or intraperitoneally injected into an animal, and then blood cell test values and biochemical test values in blood, serum, or urine collected from the animal, activity (vigor), body temperature, respiratory rate, and the like can be measured.

The term "activity (vigor)" refers to an appearance of an animal requiring medical treatment, and an activity state of the animal that is directly observed and determined by an observer (for example, a person who treats the animal). For example, the "activity" level is low inmost animals requiring medical treatment. In particular, animals which need to have a surgery for treatment have a state of activity (vigor) such as unable to move, exhausted, side lying, or lying on their stomach from before the surgery owing to a disease or the like. When "activity (vigor)" is improved by administering the ghrelin or a derivative thereof or a pharmaceutically acceptable salt thereof of the present invention to the animal for treatment, the above-mentioned state is improved compared with the state before treatment. Examples of observed changes include raising the head in response to the observer, sitting up, getting up, reacting to food, and bleating. Activity (vigor) was specifically evaluated with the following scores: 1. being lifeless (the animal is unable to move and is exhausted), 2. being slightly responsive to an external stimulus (the animal is slightly responsive to the movement of a health care professional, follows with the eyes, lifts the head, and tries to get up), 3. capable of moving in response to an external stimulus (the animal is able to get up and move in the cage although slowly), 4. as usual with normal movement, 5. more active than normal, 6. considerably more active than normal, and 7. very active (refer to D. M. Broom: J. Animal Sci., 69: 4167-75 [1991]). The expression that "activity (vigor) is improved" means that the above-mentioned score is increased after administration of ghrelin.

In the present invention, improvement of physical conditions in an animal based on parameters of blood cell test values and biochemical test values is specifically described below (refer to Lon J Rich, Interpretation of Biochemical Profiles [AAHA's 45th Annual Meeting Proceeding's, 1978]).

1. Blood Cell Test Values

White blood cells: White blood cells are known to be increased by excitation, stress, inflammation, cancer, systemic sclerosis, leukocytosis, bone marrow disorder, allergy, or the like. White blood cells are involved in biological defense by phagocytizing cells or the like, transmitting immune information, and further expressing immune competence. The white blood cell count is generally increased by bacterial infection and may be occasionally decreased by viral infection on the contrary. After administration of ghrelin, the white blood cell count was decreased along with the improvement of pathological conditions in animals which had had an increased white blood cell count due to stress, tissue inflammation, or the like before administration of ghrelin.

Platelet: Platelet is known to be increased after acute hemorrhage or by bone trauma or stress and decreased by purpura or bone marrow disorder. Platelet plays an important role to arrest hemorrhage easily. When this value is extremely decreased, hemorrhage is likely to occur. The platelet that had been decreased by pathological conditions before administration of ghrelin was increased after administration of ghrelin. The mechanism or the like of this effect is unknown.

Hemoglobin: Hemoglobin is known to be decreased by hemolytic anemia, hemolysis (drugs, renal medullary tumor, onion, etc.), inadequate production of red blood cells (RBCs), myelosuppression (antibiotics etc.), or the like. Hemoglobin is a pigment in a red blood cell that binds to oxygen. When a hemoglobin level is low, anemia occurs, and oxygen cannot be distributed to all over the body. After administration of ghrelin, the hemoglobin value was increased in animals which had had decreased hemoglobin.

2. Biochemical Test Values

Glutamic oxaloacetic transaminase (GOT): GOT is known to be increased by acute hepatitis, chronic hepatitis, liver cancer, myositis, cardiac injury, or necrosis. GOT is an enzyme that is abundant in cells of various body organs and produces amino acids. When somatic cells is broken, GOT is released from the cells, allowing a constant amount of GOT to flow in blood. Therefore, GOT in blood is increased by an organ damage. Thus, the animals in the Examples had had organ damages before administration of ghrelin, and any damage of these organs was improved after administration of ghrelin.

Glutamic pyruvic transaminase (transferase) (GPT): GPT is an enzyme abundant in hepatocytes. The blood GPT value is therefore increased abnormally when hepatocytes are injured (destroyed). Since GPT is present in cardiac muscle and skeletal muscle in addition to hepatocytes as with GOT, GPT is used as an indicator of a disease in these organs. However, GPT is less than GOT in quantity, and the degree of the increase is therefore mild.

Thus, the animals in the Examples had had injuries in the liver, cardiac muscle, or skeletal muscle before administration of ghrelin, and any injury in these organs was improved after administration of ghrelin.

Total cholesterol (T-CHO): T-CHO is known to be increased by hemolysis, glycosuria, severe nephrosis, high fat diet, biliary obstruction, hypothyroidism, or the like. In the animals in the Examples, the total protein value was unchanged, and the BUN value was high. These animals were considered to have a decreased renal function.

After administration of ghrelin, the T-CHO value was decreased (improved) in the animals in the Examples. The T-CHO value may have been improved along with a return of the renal function to normal.

Alkaline phosphatase (ALP): ALP is one of enzymes involved in the energy metabolism and is present in virtually all organs and tissues. ALP is abundant particularly in biliary cells. When these cells are injured, ALP is leaked out of the cells, and the blood ALP value is therefore increased. Thus, the animals in the Examples had had a high ALP value with injuries in the organs including the biliary system, and the ALP value was decreased after administration of ghrelin.

Blood urea nitrogen (BUN): BUN is a measure of nitrogen contained in urea. Urea in blood is transported to the kidneys, filtered by the glomerulus, and excreted in urine. If the excretion function of the kidneys is decreased, urea nitrogen is not well excreted in urine, and urea nitrogen in blood is increased.

In the Examples, the animals which had had an increased BUN value before administration of ghrelin had renal dysfunction. After administration of ghrelin, the renal function was improved.

Creatinine (Cre) (CRE): CRE is produced from a substance called creatine in muscles, appears in blood, is filtered by the glomerulus in the kidneys, and is excreted in urine. Thus, when the renal function is decreased, the blood creatinine concentration is increased. Since the CRE value is hardly affected outside the kidneys, the CRE value is considered to reflect an impaired renal function accurately. The animals in the Examples had had a decreased renal function before administration of ghrelin. The renal function was improved after administration of ghrelin.

Blood ammonia ($NH_3$): Blood $NH_3$ is known to be increased by hepatopathy, portocaval shunt syndrome, or the like. Since ammonia is a harmful substance and causes disturbance of consciousness, blood ammonia is measured to determine pathological conditions during hepatic coma or the like. The animals in the Examples had had a high blood ammonia value before administration of ghrelin. The blood ammonia was decreased after administration of ghrelin. The mechanism of this effect is unknown.

Total bilirubin (T-bil): T-bil is known to be increased by hepatocellular damage, biliary obstruction, or jaundice. Bilirubin is a pigment produced from hemoglobin. When red blood cells come to the end of their life of approximately 120 days, hemoglobin is degraded, and indirect bilirubin is produced. Indirect bilirubin is converted to direct bilirubin by actions of enzymes in the liver. Direct bilirubin is excreted into the biliary tract as a component of the bile and finally into feces. The sum of indirect bilirubin and direct bilirubin is referred to as total bilirubin. Jaundice makes the body yellow because of increase in this bilirubin pigment. The T-bil value may have been increased in the animals in the Examples before administration of ghrelin because red blood cells were damaged. After administration of ghrelin, the pathological conditions were improved, and the T-bil value was decreased.

Creatinine phosphokinase (CPK): CPK is an enzyme that is abundant in muscles and plays an important role in the energy metabolism of muscle cells. If the muscle is injured, the blood creatine kinase value is increased. The animals in the Examples had had an injury in the muscle before administration of ghrelin. The muscle injury was improved after administration of ghrelin.

C-reactive protein (CRP): If an inflammatory disease is present, the CRP value is increased as the inflammation or tissue destruction becomes severer, and is rapidly decreased as the inflammation or destruction is reduced. Therefore, examination of CRP is essential to determine the activity or change, severity, and prognosis of the pathological condition. The animals in the Examples had had severe inflammation before administration of ghrelin. The inflammation was improved in some degree after administration of ghrelin.

Serum potassium (K): Potassium is one of electrolytes that are important for maintenance and regulation of life activity and aids nervous excitation or cardiac muscle (muscle of the heart). The blood potassium value is changed by release of potassium from the intracellular fluid, filtration and reabsorption of potassium in the kidneys, or the like. 90% of potassium in the body is excreted in urine. Therefore, if the renal function is decreased because of renal failure or the like, the urinary volume is decreased, and the blood potassium value is increased. Furthermore, when severe diarrhea or vomiting occurs, the blood potassium value is decreased because potassium is eliminated out of the body with vomitus or feces. In the animals in the Examples, poor physical conditions had persisted for a relatively long period, and the serum potassium value was decreased. The serum potassium value was improved after administration of ghrelin. The mechanism of this effect is unknown.

In the present invention, body temperature as an evaluation parameter is preferably improved from hyperthermia or hypothermia, more preferably improved from hyperthermia as described below. Hyperthermia (pyrexia) is caused by an infection, dehydration, a chronic inflammatory disease, hypermetabolism, anemia, pregnancy, systemic sclerosis, meningitis, infectious endocarditis, sepsis, acute purulent cholangitis, malignant syndrome, influenza, bacterial pneumonia, *Mycoplasma* pneumonia, psittacosis, acute tonsillitis, bacterial meningitis, acute hepatitis, liver abscess, cholelithiasis, cholecystitis, cholangitis, appendicitis, uterine adnexitis, acute pyelonephritis, acute prostatitis, acute leukemia, common cold, acute pharyngitis, lung tuberculosis, *Chlamydia pneumoniae* pneumonia, renal cancer, malignant tumor, Crohn's disease, endometritis, systemic erythematosus, polymyositis, dermatomyositis, brucellosis, malaria, Hodgkin's disease, biliary atresia, polyneuritis, spinal cord disorder, Felty syndrome (Felty disease), rheumatoid arthritis, splenomegaly, or the like. Furthermore, hyperthermia is also caused by heat stroke, rhabdomyolysis, or drug allergy. Hyperthermia is also caused by stillbirth, dystocia, pyometra, and surgical removal of a reproductive organ. In the animals in the Examples which had had hyperthermia before administration of ghrelin, the body temperature was decreased after administration of ghrelin. The body temperature was considered to be decreased by improvement of a specific factor such as an infection (Merck Manual of Medical Information: Home Edition [2004]). Furthermore, feline is known to have frequent infections with virus or the like and experiences pyrexia caused by the following conditions: a viral infection of the upper respiratory tract, an infectious upper respiratory tract disease, viral rhinotracheitis, calicivirus infection, panleukopenia (parvovirus), leukemia virus infection, lymphosarcoma in the small intestine, acute lymphoid blast phase leukemia, AIDS, coronavirus infection, infectious peritonitis, intestinal coronavirus infection, herpes virus infection, reovirus infection, rotavirus infection, poxvirus infection, giant cell-forming virus infection, Aujeszky's disease, astrovirus infection, bornavirus infection, West Nile virus infection, SARS coronavirus infection, spongy encephalosis, *Bordetella bronchiseptica* infection, coliform infection, *Salmonella* infection, campylobacter infection, pasteurella infection, leptospira, *Clostridium botulinum* poisoning, actinomycosis, group G streptococcal infection, plague, *Helicobacter pylori* infection, tularemia, mycobacterial infection, tuberculosis, leprosy, atypical mycobacteriosis, mycoplasmal conjunctivitis, Q fever (coxiellosis), bartonellosis, ehrlichiosis, *Chlamydia psittaci* infection, toxoplasmosis, cryptosporidium infection, coccidiosis, trichomoniasis, and giardiasis ("The cat: diseases and clinical management", translation supervised by Kato G and Oshima S. Buneido Publishing Co., Ltd. [1997]).

In the present invention, the respiratory rate as an evaluation parameter is preferably improved from a respiratory rate higher or lower than a usual respiratory rate, more preferably improved from a respiratory rate higher than a usual respiratory rate. A high respiratory rate means breathing rapidly. The rapid breathing generally suggests that dyspnoea has occurred. Examples of the disease causing dyspnoea include pulmonary diseases such as pneumonia and pulmonary edema, upper respiratory tract diseases such as tracheal collapse and abnormal soft palate, cardiac diseases such as cor pulmonale and filariasis, and trauma such as diaphragmatic hernia and lung hemorrhage due to a traffic accident or a fall from a height. A high respiratory rate is also caused by heat stroke. When examining such an animal, a veterinarian exercises caution not to suppress the breathing, and has to identify the cause as early as possible by performing various tests such as x-ray examination to take appropriate measures (Veterinary Internal Medicine (small animals), Bun-eido Publishing Co., Ltd., edited by Japanese College of Veterinary Internal Medicine, 2005, 1st ed., p. 104). In the animals in the Examples which had had dyspnoea with concurrent pulmonary edema, the respiratory condition was improved after administration of ghrelin.

The "degree of anger or anxiety" is an evaluation parameter indicating the degree of anger and the degree of anxiety of an animal determined by an observer who directly observes how the animal under medical treatment responds to a health care professional (a veterinarian etc.). The criteria used during medical treatment were, for example, as follows: the animal is calm; can be touched by but is unaccustomed to a health care professional; wanders around or hides in the kennel with anxiety; barely able to be touched; or too violent to be touched and tends to bite. Anger and anxiety may not be clearly distinguished from each other particularly in a canine or a feline because a canine or a feline cannot be touched by a health care professional when the canine or the feline is frightened or is angry because of pain. Therefore, the degree of anger or anxiety was established as an evaluation parameter. In the present invention, the evaluation parameter of the degree of anger or anxiety was evaluated with the following scores: 1. calm and accustomed to a health care professional, 2. able to be touched by but unaccustomed to a health care professional and restless, 3. wandering around or hiding in the kennel with anxiety, 4. barely able to be touched, 5. too violent to be touched by a health care professional and tends to bite. Improvement of the degree of anger or anxiety means that this evaluation score is decreased after administration of ghrelin. For example, a score of 5 (too violent to be touched and tends to bite) before administration is improved to a score of 2 (able to be touched by but unaccustomed to a health care professional) or the like after administration of ghrelin.

The parameters indicating the improvement of physical conditions in an animal requiring medical treatment according to the present invention will be described below in relation to major effects of ghrelin, i.e., an appetite increasing effect and a growth hormone secretagogue effect. Among general tests (evaluation parameters) such as blood cell tests and biochemical tests, tests that are affected by meal are known. Examples of parameters that are increased after meal include blood glucose and triglyceride (TG), and these values are known to be directly affected by meal (Veterinary Internal Medicine (small animals edition), Bun-eido Publishing Co., Ltd., edited by the Japanese College of Veterinary Internal Medicine, 2005, 1st ed., p. 13). Total cholesterol (T-CHO) is also known to be increased by ingestion of meal. On the other hand, parameters associated with the liver and cardiac functions, such as GOT (aspartate aminotransferase [AST]), GPT (alanine aminotransferase [ALT]), LDH, ALP, γ-GTP, CHE, CK, and bilirubin, are known not to be affected by meal (Veterinary Internal Medicine Diagnostics, Bun-eido Publishing Co., Ltd., supervising editors, Hasegawa A and Maede Y, 1997).

BUN and CRE are commonly used parameters indicating renal functions. Creatinine is hardly affected by meal compared with urea nitrogen and seemed to be a reliable indicator of renal functions (CKD Practice Guide 2009, edited by the Japanese Society of Nephrology (ISBN 978-4-88563-185-6)).

Therefore, biochemical test values (GPT, ALP, CPK, CRE, and the like) that were improved in the Examples are considered to be parameters that are not affected by meal. The BUN value, which is known to be increased by ingestion of meal, was decreased after administration of ghrelin in the test according to the present invention. This effect does not appear to be an influence of the increase in the quantity of meal.

In the present invention, high body temperature was decreased after administration of ghrelin. Since body temperature is known to be increased by meal (Jensen M. et al.: Am. J. Physiol., 268: E433-E488), this effect does not appear to be an influence of ingestion of meal.

Furthermore, many blood test values are known to be hardly affected by meal (Laboratory Test Guide 2003-2004, edited by the Medical Practice Editorial Committee, Bunkodo Co., Ltd., 2003; Kohashi R, All about tests for easy understanding of diseases and tests for diseases, Shufunotomo Co., Ltd., 2003; Nishizaki O, BOOKS of special course for nurses: Manual for reading test values, Digit Brain, Inc., 2002; and Ando Y, Manual for understanding tests at hospital, 3rd revision, Shogakkan Inc., 1999). For example, the white blood cell count may be increased transiently by ingestion of food (refer to Hematology in laboratory animals, Seki et al. ed., Soft Science Inc. [1981] p. 364), and the decrease in a high white blood cell count after administration of ghrelin does not appear to be an influence of increased food ingestion.

Therefore, since administration of ghrelin to animals under medical treatment normalized the white blood cell count, the platelet count, the body temperature, and the biochemical test values (GOT, GPT, ALP, CPK, CRP, T-Cho, T-bil, BUN, Cre, K, and ammonia), administration of ghrelin can be applied to the treatment of pathological conditions associated with high or low (platelet [PLT] and K) values of these tests. Examples of the pathological conditions treated by the therapeutic agent of the present invention include symptoms after surgery for the treatment of a disease such as a genital disease, a tumor, a urological disease, a bone disease, disc hernia, and a gastrointestinal tract disease. The therapeutic agent of the present invention is also effective for the treatment of symptoms of diseases such as lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, feline acquired immunodeficiency syndrome (FIV), feline leukemia virus (FELV) infection, canine parvovirus (CPV) infection, feline viral rhinotracheitis (FVR), a liver disease, filariasis, hemobartonellosis, babesiosis, habu bite, anaphylaxis, a falling accident, rib fracture, and burn.

In addition to the above-mentioned pathological conditions, examples of pathological conditions treated by ghrelin or a derivative thereof or a pharmaceutically acceptable salt thereof include excitation, stress, cancer, systemic sclerosis, leukocytosis, bone marrow disorders, allergy, myocardial infarction, skeletal muscle necrosis, central nervous system damage, uremia, poisoning, an immunological disease, fatty liver (obesity), a bone disease, biliary tract obstruction, myocarditis, hepatopathy, tumor, acute pancreatitis, myositis, hypothyroidism, cholestasis, diabetes, biliary obstruction, jaundice, hemolysis, renal dysfunction, urological impairment, hemorrhage, uremia, chronic renal failure, starvation, circulatory organ failure, hepatic portal venous shunts, infections, leukemia, inflammations, dehydration, chronic inflammatory diseases, hypermetabolism, anemia, pregnancy, systemic sclerosis, meningitis, infectious endocarditis, sepsis, acute purulent cholangitis, malignant syndrome, influenza, bacterial pneumonia, *Mycoplasma* pneumonia, psittacosis, acute tonsillitis, bacterial meningitis, acute hepatitis, liver abscess, cholelithiasis, cholecystitis, cholangitis, appendicitis, uterine adnexitis, acute pyelonephritis, acute prostatitis, acute leukemia, common cold, acute pharyngitis, lung tuberculosis, *Chlamydia pneumoniae* pneumonia, renal cancer, malignant tumor, Crohn's disease, endometritis, systemic erythematosus, polymyositis, dermatomyositis, brucellosis, malaria, Hodgkin's disease, biliary atresia, polyneuritis, spinal cord disorder, Felty syndrome (Felty disease), rheumatoid arthritis, and splenomegaly.

Furthermore, in the test according to the present invention, the white blood cell count was decreased. However, ghrelin is known to have a growth hormone secretagogue effect (Non Patent Literature 1), and growth hormone is known to affect the white blood cell count. Specifically, increase in white blood cell count has been reported as an adverse drug reaction of administration of growth hormone (Precautions of Genotropin [trade name] revision No. 08-17). This effect is opposite of the results of the test according to the present invention, and the effect in the present invention does not appear to be an action of growth hormone.

Furthermore, since one or more of activity (vigor), blood cell test values, biochemical test values, and body temperature were improved in many of the animals which did not ingest food after administration of ghrelin in the present invention, an improvement effect of administration of ghrelin, not an influence of food ingestion, was demonstrated.

From the above, the improvement in parameters shown in the tests according to the present invention did not appear to have resulted from the increased quantity of meal caused by the appetite increasing effect and the growth hormone secretagogue effect, which are the major effects of ghrelin, or from the increased growth hormone secretion.

In the present invention, preferred examples of a combination of a reason for medical treatment and an evaluation parameter include the following combinations:

1) the reason for the medical treatment is pyometra or surgical removal of a reproductive organ, and the evaluation parameters is vigor, white blood cell count, hemoglobin value, or platelet count, which are blood cell test values, GPT or CRP, which are biochemical test values, or body temperature;

2) the reason for the medical treatment is mammary gland tumor, and the evaluation parameter is vigor, white blood cell count, hemoglobin value, or platelet count, which are blood cell test values, GPT, which is a biochemical test value, or body temperature;

3) the reason for the medical treatment is a fracture or an accident, and the evaluation parameter is vigor, or GOT, GPT and/or creatinine value, which are biochemical test values;

4) the reason for the medical treatment is urethral opening formation, and the evaluation parameter is vigor, platelet count and/or white blood cell count, which are blood cell test values, or creatinine value, which is a biochemical test value;

5) the reason for the medical treatment is stillbirth or dystocia, and the evaluation parameter is body temperature;

6) the reason for the medical treatment is an infection, and the evaluation parameter is vigor, white blood cell count, which is a blood cell test value, or serum potassium value, GOT, and/or GPT, which are biochemical test values;

7) the reason for the medical treatment is renal dysfunction, and the evaluation parameter is vigor, white blood cell count, which is a blood cell test value, or ALP and/or CPK, which are biochemical test values;

8) the reason for the medical treatment is anaphylaxis, and the evaluation parameter is vigor or serum ammonia value, which is a biochemical test value;

9) the reason for the medical treatment is a genital disease, such as pyometra or surgical removal of a reproductive organ, and the evaluation parameter is one or more of BUN and CRP, which are biochemical test values, body temperature, and activity (vigor);

10) the reason for the medical treatment is a tumor, such as mammary gland tumor, ovarian cyst, testicle tumor, salivary gland cyst, or liver tumor mass, and the evaluation parameter is one or more of activity (vigor), body temperature, and the degree of anger or anxiety;

11) the reason for the medical treatment is an orthopedic disease, such as a fracture, an accident, luxation, or disc hernia, and the evaluation parameter is one or more of body temperature, the degree of anger or anxiety, respiratory rate, activity (vigor), and GOT, GPT, BUN, and CPK, which are biochemical test values;

12) the reason for the medical treatment is a renal dysfunction, such as urinary retention, cystolithiasis, or renal failure, and the evaluation parameter is one or more of white blood cell count and platelet count, which are blood cell test values, creatinine (Cre) value, which is a biochemical test value, and activity (vigor);

13) the reason for the medical treatment is an infection or an parasitism, and the evaluation parameter is one or more of BUN, which is a biochemical test value, respiratory rate, and activity (vigor);

14) the reason for the medical treatment is an inflammatory disease, such as dermatitis, bite, or laceration, and the evaluation parameter is one or more of body temperature, activity (vigor), and GOT, GPT, and BUN, which are biochemical test values; and 15) the reason for the medical treatment is a digestive system disease, such as vomiting, diarrhea, malnutrition, debility, ileus, or intussusception, and the evaluation parameter is activity (vigor).

Examples of a substance that can be used in the present invention include substances having an activity of increasing an intracellular calcium ion concentration by acting on a growth hormone secretagogue receptor (GHS-R).

The growth hormone secretagogue receptor is a receptor to which a growth hormone secretagogue (GHS) binds, and subtypes such as the GHS-R1a and the GHS-R1b are known to exist. Of these subtypes, only the GHS-R1a is known to activate a receptor involved in phospholipase C-related signal transduction and thereby increase intracellular calcium. In the present specification, the term "growth hormone secretagogue receptor (GHS-R)" refers to the GHS-R1a unless otherwise specified.

Whether a substance "has an activity of increasing an intracellular calcium ion concentration" by acting on the GHS-R can be easily determined by measuring an intracellular calcium ion concentration conveniently with a known technique. For example, a fluorometric imaging plate reader (FLIPR, Molecular Devices) using changes in fluorescence intensity of Fluo-4 AM (Molecular Probes) caused by changes in the calcium ion concentration can be used. Furthermore, whether a peptide having an activity of increasing intracellular calcium concentration has a growth hormone secretagogue activity can be determined in vitro or in vivo with a known technique. For example, a substance is added to cells that have been confirmed to secrete growth hormone and express the GHS-R (for example, brain pituitary gland cells), and then growth hormone secreted in the cell culture broth can be measured in vitro by radioimmunoassay using an anti-growth hormone antibody. To determine a growth hormone secretagogue activity in vivo, a peptide having an activity of increasing intracellular calcium concentration is injected into a peripheral vein of an animal, and then the growth hormone concentration in serum can be measured. Any substance can be used as long as the substance is confirmed to increase a calcium concentration by any of the above-mentioned methods.

Particularly preferred examples of the substance that can be used in the present invention include ghrelin or a derivative thereof or a pharmaceutically acceptable salt thereof. Examples of ghrelin or a derivative thereof or a pharmaceutically acceptable salt thereof and a method for production thereof are described in Patent Literature 1 and others.

In the present specification, "ghrelin" is ghrelin derived from various useful animals, such as, for example, canine, feline, rat, mouse, porcine, bovine, equine, chicken, deer, and human, and, in particular, refers to a peptide compound in which a side chain hydroxyl group of the amino acid residue at the 3rd position from the N terminus of a peptide having any one of sequences of SEQ ID NOS: 1 to 23 is acylated with a fatty acid. The number of carbon atoms in the fatty acid is preferably 2, 4, 6, 8, 10, 12, 14, 16, or 18. The number of carbon atoms is particularly preferably 8 (an octanoyl group). The fatty acid may be straight or branched and may be saturated or unsaturated.

In the present specification, the "ghrelin derivative" is a peptide compound which has an amino acid sequence including deletion, substitution, and/or addition of an amino acid in an amino acid sequence according to the above-mentioned ghrelin and has an activity of increasing an intracellular calcium ion concentration by acting on the GHS-R. A ghrelin derivative is preferably a peptide compound that has an amino acid sequence including deletion, substitution, and/or addition of one to several amino acids between the amino acid residue at the 5th position from amino terminus and the amino acid residue of the carboxy terminus in an amino acid sequence according to the above-mentioned ghrelin (for example, between the amino acid residue at the 5th position and the amino acid residue at the 28th position from the amino terminus of an amino acid sequence of SEQ ID NO: 1, 4, 6, 7, 8, 10, 14, 16, 20, 21, 22, or 23, between the amino acid residue at the 5th position and the amino acid residue at the 27th position from the amino terminus of an amino acid sequence of SEQ ID NO: 2, 3, 5, 8, 9, 15, 17, 18, or 19, between the amino acid residue at the 5th position and the amino acid residue at the 26th position from the amino terminus of an amino acid sequence of SEQ ID NO: 13, and between the amino acid residue at the 5th position and the amino acid residue at the 24th position from the amino terminus of an amino acid sequence of SEQ ID NO: 11 or 12), and has an activity of increasing an intracellular calcium ion concentration by acting on a growth hormone secretagogue receptor (GHS-R). Furthermore, the number of amino acids deleted or the like in the "amino acid sequence including deletion, substitution, and/or addition of one to several amino acids" is not particularly limited as long as a peptide compound having the amino acid sequence has a desired function, and examples of the number of amino acids deleted or the like include one to nine, preferably approximately one to four. It is considered that substitution of many amino acids with an amino acid having a similar property (electric charge and/or polarity) or the like does not cause loss of a desired function. Furthermore, the amino acid sequence of a ghrelin derivative preferably has a homology of 70%, preferably 80%, more preferably 90%, particularly preferably 95%, most preferably 97% comparing with a naturally occurring amino acid sequence. Ghrelins derived from other animals (SEQ ID NOS: 2 to 23) have similar characteristics.

Other ghrelin derivatives can be easily designed by, for example, using descriptions in the above-mentioned Patent Literature 1 as reference.

In each (individual) animal requiring medical treatment, ghrelin derived from the same species as the animal is preferably used. For example, a canine-derived ghrelin is preferably used in a canine. The canine-derived ghrelin is a peptide compound having an amino acid sequence of SEQ ID NO: 1 consisting of 28 amino acids in which a side chain hydroxyl group of the serine residue at the 3rd position from the amino terminus of the sequence is acylated with a fatty acid (an n-octanoyl group). However, since a ghrelin derivative can also be used in the present invention, ghrelin that is not derived from the same species as the animal to be treated can be used. For example, a canine-derived ghrelin can be used in a feline. A feline-derived ghrelin is a peptide compound having an amino acid sequence of SEQ ID NO: 3 consisting of 27 amino acids in which a side chain hydroxyl group of the serine residue at the 3rd position from the amino terminus of the sequence is acylated with a fatty acid (an n-octanoyl group). Therefore, the amino acid sequence of SEQ ID NO: 3 is different from the canine-derived ghrelin of SEQ ID NO: 1 in terms of two amino acids and from the canine-derived ghrelin of SEQ ID NO: 2 in terms of one amino acid. However, these canine-derived ghrelins can be used in felines. This is applicable to other animals.

The ghrelin and a derivative thereof according to the present invention can be obtained by a usual method (for example, refer to J. Med. Chem., 43, pp. 4370-4376, 2000; Patent Literature 1). The ghrelin and a derivative thereof according to the present invention can be isolated from a natural raw material or can be produced by recombinant DNA technology and/or chemical synthesis. Furthermore, if a peptide compound such as ghrelin and a derivative thereof requires modification (acylation) of an amino acid residue, the peptide compound can be subjected to a modification reaction by known means. For example, in a production method using recombinant DNA technology, the peptide compound of the present invention can be obtained by culturing a host cell transformed with an expression vector having a DNA encoding the peptide compound according to the present invention and collecting a target peptide compound from the culture. By selecting an appropriate host cell, a modified (acylated) target peptide compound can be obtained in the cell.

Furthermore, if the peptide is not modified (acylated), a modification reaction, such as acylation, can be performed according to known means as required.

Examples of the vector incorporating a gene include *Escherichia coli* vectors (pBR322, pUC18, pUC19, etc.), *Bacillus subtilis* vectors (pUB110, pTP5, pC194, etc.), yeast vectors (types YEp, YRp, and YIp), and animal cell vectors (retrovirus, vaccinia virus, etc.). Any other vector can be used as long as the vector can harbor a target gene in the host cell stably. The vector is introduced into a suitable host cell. Examples of a method for incorporating a target gene into a plasmid and a method for introducing the plasmid into a host cell include methods described in Molecular Cloning (Sambrook et al., 1989).

For expression of a target peptide gene in the above-mentioned plasmid, a promoter is linked upstream of the gene so that the promoter functions.

Any promoter can be used in the present invention as long as the promoter is suitable for a host cell used to express a target gene. For example, when a host cell to be transformed belongs to the genus *Escherichia*, the lac promoter, the trp promoter, the lpp promoter, the λPL promoter, the recA promoter, and the like can be used. When the host cell belongs to the genus *Bacillus*, the SPO1 promoter, the SPO2 promoter, and the like can be used. When the host cell is a yeast, the GAP promoter, the PHO5 promoter, the ADH promoter, and the like can be used. When the host cell is an animal cell, the SV40-derived promoter, the retrovirus-derived promoter, and the like can be used.

A host cell is transformed with a vector having a target gene obtained as described above. Examples of the host cell include bacteria (for example, bacteria belonging to the genus *Escherichia* or *Bacillus*), yeasts (yeasts belonging to the genera *Saccharomyces, Pichia, Candida*, etc.), and animal cells (CHO cells, COS cells, etc.). A liquid medium is appropriate for culture. The medium particularly preferably contains carbon sources, nitrogen sources, and the like required to grow transformed cells cultured in the medium. Vitamins, growth promoting factors, serum, and the like can be added as required.

To directly produce a peptide modified (acylated) with a fatty acid, it is preferable to use a cell that has a processing protease activity that can excise a precursor polypeptide of the peptide at an appropriate position and an activity of acylating a serine residue in the peptide. A host cell having such a processing protease activity and a serine acylating activity can be selected by transforming a host cell with an expression vector having cDNA encoding the precursor polypeptide and confirming that the transformed cell produces a fatty acid-modified peptide having a calcium-increasing activity or a growth hormone secretagogue activity.

After culture, the peptide according to the present invention is isolated from the culture and purified by a usual method. For example, to extract a target substance from a cultured bacterial cell or a cell, bacterial cells or cells are collected after culture, suspended in a buffer containing a protein denaturant (guanidine hydrochloride etc.), and crushed by ultrasonication or the like, and then the suspension is centrifuged. Then, a target substance from the supernatant can be purified by suitably using a combination of isolation and purification methods, such as gel filtration, ultrafiltration, dialysis, SDS-PAGE, and various chromatography techniques, taking into account molecular weight, solubility, charge (isoelectric point), affinity, and the like of the target substance.

The ghrelin and a derivative thereof according to the present invention can be chemically synthesized by a usual method. For example, the ghrelin and a derivative thereof according to the present invention is obtained by condensing an amino acid containing a protective group by a liquid phase technique and/or a solid phase technique to elongate a peptide chain, removing all protective groups with an acid, and purifying the obtained crude product by the above-mentioned purification methods. A side chain of an amino acid at a selectively targeted position can also be acylated with an acylating enzyme or an acyl group transferase.

Furthermore, various conventional methods for producing a peptide are known. The peptide according to the present invention can also be produced easily by a known method, such as, for example, a classic peptide synthesis method or a solid phase method.

Furthermore, a production method employing recombinant DNA technology and a chemical synthesis in combination may be used. The peptide according to the present invention can be produced by a method comprising producing a fragment containing a modified amino acid residue by chemical synthesis, producing other fragments not containing the modified amino acid residue by recombinant DNA technology, and then fusing these fragments (refer to Patent Literature 1).

Salts of ghrelin or a derivative thereof, which are substances acting on the GHS-R1a that can be used in the present invention, are preferably pharmaceutically acceptable salts. Examples of the salts include salts with an inorganic base, salts with an organic base, salts with an inorganic acid, salts with an organic acid, and salts with a basic or acidic amino acid.

Preferred examples of salts with an inorganic base include alkali metal salts, such as sodium salts and potassium salts; alkaline earth metal salts, such as calcium salts and magnesium salts; aluminium salts, and ammonium salts.

Preferred examples of salts with an organic base include salts with trimethylamine, triethylamine, pyridine, picoline, ethanolamine, diethanolamine, triethanolamine, dicyclohexylamine, N,N'-dibenzylethylenediamine, or the like.

Preferred examples of salts with an inorganic acid include salts with hydrochloric acid, hydrobromic acid, nitric acid, sulfuric acid, phosphoric acid, or the like.

Preferred examples of salts with an organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, or the like.

Preferred examples of salts with a basic amino acid include salts with arginine, lysine, ornithine, or the like. Preferred examples of salts with an acidic amino acid include salts with aspartic acid, glutamic acid, or the like.

Of the above salts, sodium salts and potassium salts are most preferred.

The agent according to the present invention, which contains ghrelin or a derivative thereof or a pharmaceutically acceptable salt thereof as an active ingredient, can be used in an animal (for example, canine, feline, mouse, rat, rabbit, bovine, equine, porcine, or monkey) as a mixture with a pharmaceutically acceptable carrier, diluent, extender, and the like.

A predetermined dose of the agent of the present invention is preferably administered to an animal under medical treatment parenterally, for example, by intravenous, subcutaneous, intramuscular, or intraperitoneal injection as a single dose or divided doses. When the animal is a companion animal and particularly is treated at home, transnasal administration, pulmonary administration, suppository administration, and instillation are preferred in addition to the subcutaneous or intramuscular injection.

In the present invention, the dose of the agent is not particularly limited and can be suitably selected depending on the intended use; the age, body weight, type, symptoms, or conditions of a target animal; a concomitant agent; and the like. When a single dose or several doses are administered to a mature animal, ghrelin or a derivative thereof or a pharmaceutically acceptable salt thereof as an active ingredient is preferably administered at a dose of 0.001 to 100 mg, more preferably 0.01 to 10 mg.

The above-mentioned dose is preferably administered once to several times daily for about one day to one or two weeks, more preferably for about two days to one week.

Examples of pharmaceutically acceptable carriers include various commonly used organic or inorganic carrier substances as preparation materials, and such a substance is added as a diluent, a lubricant, a binder, or a disintegrating agent in a solid preparation; or a solvent, a dissolving aid, a suspending agent, an isotonizing agent, a buffer, or a soothing agent in a liquid preparation, or the like.

Furthermore, excipients for a preparation such as a preservative, an antioxidant, a coloring material, and a sweetener can also be used as required.

Preferred examples of the diluent include lactose, sucrose, D-mannitol, starch, crystalline cellulose, and light anhydrous silicic acid.

Preferred examples of the lubricant include magnesium stearate, calcium stearate, talc, and colloidal silica.

Preferred examples of the binder include crystalline cellulose, sucrose, D-mannitol, dextrin, hydroxypropylcellulose, hydroxypropylmethylcellulose, and polyvinylpyrrolidone.

Preferred examples of the disintegrating agent include starch, carboxymethylcellulose, carboxymethylcellulose calcium, croscarmellose sodium, and carboxymethyl starch sodium.

Preferred examples of the solvent include water for injection, alcohols, propylene glycol, macrogol, sesame oil, and corn oil.

Preferred examples of the dissolving aid include polyethylene glycol, propylene glycol, D-mannitol, benzyl benzoate, ethanol, Tris-aminomethane, cholesterol, triethanolamine, sodium carbonate, and sodium citrate.

Preferred examples of the suspending agent include surfactants such as stearyl triethanolamine, sodium lauryl sulfate, lauryl aminopropionate, lecithin, benzalkonium chloride, benzethonium chloride, and glycerine monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose.

Preferred examples of the isotonizing agent include sodium chloride, glycerine, and D-mannitol.

Preferred examples of the buffer include buffers such as phosphates, acetates, carbonates, and citrates.

Preferred examples of the soothing agent include benzyl alcohol.

Preferred examples of the preservative include paraoxybenzoate esters, chlorobutanol, benzyl alcohol, phenethyl alcohol, dehydroacetic acid, and sorbic acid.

Preferred examples of antioxidants include sulfites and ascorbic acid.

The dosage forms of the medicinal or therapeutic agent of the present invention are preferably dosage forms suitable for oral administration. Examples of dosage forms suitable for oral administration include syrup, tablet, and capsule.

The dosage forms of the medicinal or therapeutic agent of the present invention are preferably dosage forms suitable for parenteral administration. Examples of dosage forms suitable for parenteral administration include an injection for intravenous administration, intracutaneous administration, subcutaneous administration, intramuscular administration, or the like, a drip infusion, a suppository, an eye drop, a percutaneous absorbent, a transmucosal absorbent, and an inhalant. The above-mentioned injections are preferred as a dosage form. Particularly when the animal is an adult canine and is treated at home, dosage forms such as transmucosal absorbent, inhalant, suppository, and eye drop are also preferred. Various agents of these dosage forms are known to those skilled in the art, and those skilled in the art suitably select a dosage form suitable for a required administration route. A medicinal composition or a therapeutic agent can be produced using one or more excipients for a preparation that can be used in the field, as required.

For example, a medicinal or therapeutic agent in the form of injection, drip infusion, or eye drop can be provided by dissolving ghrelin, which is a substance acting on the GHS-R1a, as an active ingredient in distilled water for injection together with one or more excipients for a preparation such as an appropriate buffer, a sugar solution, an isotonizing agent, a pH modifier, a soothing agent, and a preservative, sterilizing the mixture by filtration (with a filter), and then filling the solution into an ampoule or a vial, or lyophilizing the solution sterilized by filtration to prepare a lyophilized preparation.

Examples of excipients that can be used include saccharides such as glucose, mannitol, xylitol, and lactose; hydrophilic polymers such as polyethylene glycol; alcohols such as glycerol; amino acids such as glycine; proteins such as serum albumin; salts such as NaCl and sodium citrate; acids such as acetic acid, tartaric acid, and ascorbic acid; surfactants such as Tween 80; and reducing agents such as sodium sulfite. Such preparations can be used as an injection or a drip infusion agent after dissolved in distilled water for injection or physiological saline added thereto. Furthermore, nasal agents such as a nasal drop or a nasal spray (intranasal administration) and the like are also suitable for transmucosal administration. An inhalant is also suitable for pulmonary administration.

The content of ghrelin or a derivative thereof or a pharmaceutically acceptable salt thereof in each preparation is preferably 0.001 to 100 mg, more preferably 0.01 to 10 mg. The agent of the present invention contains preferably 0.001 to 100 mg, more preferably 0.01 to 10 mg per dose unit of ghrelin or a derivative thereof or a pharmaceutically acceptable salt thereof as an active ingredient. The preparation is preferably administered once to several times daily.

The present invention includes the following embodiments.

(1) A therapeutic agent for accelerating recovery for animal use to accelerate the improvement of physical conditions in an animal under medical treatment, which contains ghrelin or a derivative thereof as an active ingredient and improves one or more of evaluation parameters consisting of activity (vigor), blood cell test values, biochemical test values, and body temperature.
(2) The therapeutic agent for accelerating recovery according to the above (1), wherein the animal is an animal after surgery.
(3) The therapeutic agent for accelerating recovery according to the above (1) or (2), wherein the blood cell in the blood cell test values is white blood cell, platelet, or hemoglobin.
(4) The therapeutic agent for accelerating recovery according to anyone of the above (1) to (3), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), C-reactive protein (CRP), or serum potassium (K).
(5) The therapeutic agent for accelerating recovery according to any one of the above (1) to (4), wherein the animal is an animal after surgery for the treatment of a disease selected from a genital disease, a tumor, an urological disease, a bone disease, disc hernia, and a gastrointestinal tract disease.
(6) The therapeutic agent for accelerating recovery according to any one of the above (1) to (4), wherein the animal is an animal under medical treatment for a disease selected from lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, feline acquired immunodeficiency syndrome (FIV), feline leukemia virus (FELV) infection, canine parvovirus (CPV) infection, feline viral rhinotracheitis (FVR), a liver disease, filariasis, hemobartonellosis, babesiosis, habu bite, anaphylaxis, a falling accident, rib fracture, and burn.
(7) The therapeutic agent for accelerating recovery according to any one of the above (1) to (6), wherein a combination of a reason for medical treatment and an evaluation parameter is one of the following combinations: 1) the reason for the medical treatment is pyometra or surgical removal of a reproductive organ, and the evaluation parameter is improvement of body temperature; 2) the reason for the medical treatment is mammary gland tumor, and the evaluation parameter is improvement of vigor; 3) the reason for the medical treatment is a fracture or an accident, and the evaluation parameter is improvement of vigor or improvement of GOT, GPT and/or creatinine value, which are biochemical test values; 4) the reason for the medical treatment is urethral opening formation, and the evaluation parameter is improvement of platelet count and/or white blood cell count, which are blood cell test values, or improvement of creatinine value, which is a biochemical test value; 5) the reason for the medical treatment is stillbirth or dystocia, and the evaluation parameter is improvement of body temperature; 6) the reason for the medical treatment is an infection, and the evaluation parameter is improvement of vigor, stabilization of a high respiratory rate, or improvement of serum potassium value or GOT and/or GPT, which are biochemical test values; 7) the reason for the medical treatment is renal dysfunction, and the evaluation parameter is vigor, improvement of white blood cell count, which is a blood cell test value, or improvement of ALP and/or CPK, which are biochemical test values; 8) the reason for the medical treatment is anaphylaxis, and the evaluation parameter is vigor or serum ammonia value, which is a biochemical test value.
(8) The therapeutic agent for accelerating recovery according to any one of the above (1) to (7), wherein the ghrelin or a derivative thereof is a peptide, or a pharmaceutically acceptable salt thereof, selected from the group consisting of (i) a peptide which has any one of amino acid sequences of SEQ ID NOS: 1 to 23, the amino acid residue at the 3rd position from the amino terminus is a modified amino acid residue containing a fatty acid introduced into a side chain thereof and (ii) a peptide which has an amino acid sequence including deletion, substitution, and/or addition of one to several amino acids in an amino acid sequence between the amino acid residue at the 5th position and the amino acid residue at the 28th position from the amino terminus in any one of amino acid sequences of SEQ ID NOS: 1 to 23, and the amino acid residue at the 3rd position from the amino terminus is a modified amino acid residue containing a fatty acid introduced into a side chain thereof, and has an action of increasing intracellular calcium concentration by acting on a GHS receptor.

The ghrelin or a derivative thereof used in the present invention may be a peptide having the above-mentioned amino acid sequences. Specifically, other amino acids may be added to the N terminus.

(9) The therapeutic agent for accelerating recovery according to the above (8), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.
(10) The therapeutic agent for accelerating recovery according to the above (9), wherein the ghrelin is a peptide that has an amino acid sequence of SEQ ID NO: 1 in which the side chain hydroxyl group of the serine residue at the 3rd position from the amino terminus is acylated with an n-octanoyl group.
(11) The therapeutic agent for accelerating recovery according to any one of the above (1) to (10), which contains 0.001 to 100 mg per dose unit of ghrelin or a derivative thereof as an active ingredient.
(12) A treatment method for accelerating the improvement of a physical condition in an animal under medical treatment, comprising administration of ghrelin or a derivative thereof to the animal under medical treatment to improve one or more of evaluation parameters consisting of activity (vigor), blood cell test values, biochemical test values, and body temperature of the animal.

(13) The treatment method according to the above (12), wherein the animal is an animal after surgery.

(14) The treatment method according to the above (12) or (13), wherein the blood cell in the blood cell test values is white blood cell, platelet, or hemoglobin.

(15) The treatment method according to any one of the above (12) to (14), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), C-reactive protein (CRP), or serum potassium (K).

(16) The treatment method according to any one of the above (12) to (15), wherein the animal is an animal after surgery for the treatment of a disease selected from a genital disease, a tumor, a urological disease, a bone disease, disc hernia, and a gastrointestinal tract disease.

(17) The treatment method according to any one of the above (12) to (15), wherein the animal is an animal under medical treatment for a disease selected from lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, feline acquired immunodeficiency syndrome (FIV), feline leukemia virus (FELV) infection, canine parvovirus (CPV) infection, feline viral rhinotracheitis (FVR), a liver diseases, filariasis, hemobartonellosis, babesiosis, habu bite, anaphylaxis, a falling accident, rib fracture, and burn.

(18) The treatment method according to any one of the above (12) to (17), wherein a combination of a reason for medical treatment and an evaluation parameter is one of the following: 1) the reason for the medical treatment is pyometra or surgical removal of a reproductive organ, and the evaluation parameter is improvement of body temperature; 2) the reason for the medical treatment is mammary gland tumor, and the evaluation parameter is improvement of vigor; 3) the reason for the medical treatment is a fracture or an accident, and the evaluation parameter is improvement of vigor or improvement of GOT, GPT, and/or creatinine value, which are biochemical test values; 4) the reason for the medical treatment is urethral opening formation, and the evaluation parameter is improvement of platelet count and/or white blood cell count, which are blood cell test values, or improvement of creatinine value, which is a biochemical test value; 5) the reason for the medical treatment is stillbirth or dystocia, and the evaluation parameter is improvement of body temperature; 6) the reason for the medical treatment is an infection, and the evaluation parameter is improvement of vigor, stabilization of a high respiratory rate, or improvement of serum potassium value, or improvement GOT and/or GPT which are biochemical test values; 7) the reason for the medical treatment is renal dysfunction, and the evaluation parameter is vigor, improvement of white blood cell count, which is a blood cell test value, or improvement of ALP and/or CPK, which are biochemical test values; and 8) the reason for the medical treatment is anaphylaxis, and the evaluation parameter is vigor or serum ammonia value, which is a biochemical test value.

(19) The treatment method according to any one of the above (12) to (18), wherein the ghrelin or a derivative thereof is a peptide, or a pharmaceutically acceptable salt thereof, selected from the group consisting of (i) a peptide which has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide which has an amino acid sequence including deletion, substitution, and/or addition of one to several amino acids in an amino acid sequence between the amino acid residue at the 5th position and the amino acid residue at the 28th position from the amino terminus in any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.

(20) The treatment method according to the above (19), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.

(21) The treatment method according to the above (20), wherein the ghrelin is a peptide that has an amino acid sequence of SEQ ID NO: 1 in which the side chain hydroxyl group of the serine residue at the 3rd position from the amino terminus is acylated with an n-octanoyl group.

(22) The treatment method according to anyone of the above (12) to (21), wherein a dose of 0.001 to 100 mg of ghrelin or a derivative thereof is administered as an active ingredient.

(23) Use of ghrelin or a derivative thereof for production of a therapeutic agent for accelerating recovery for animal use to accelerate the improvement of physical conditions in an animal under medical treatment, which improves one or more of evaluation parameters consisting of activity (vigor), blood cell test values, biochemical test values, and body temperature.

(24) The use according to the above (23), wherein the animal is an animal after surgery.

(25) The use according to the above (23) or (24), wherein the blood cell of the blood cell test values is white blood cell, platelet, or hemoglobin.

(26) The use according to any one of the above (23) to (25), wherein the biochemical test value is the value of glutamic pyruvic transaminase (GPT), glutamic oxaloacetic transaminase (GOT), total cholesterol (T-CHO), alkaline phosphatase (ALP), blood urea nitrogen (BUN), serum creatinine (Cre), blood ammonia ($NH_3$), total bilirubin (T-bil), creatinine phosphokinase (CPK), C-reactive protein (CRP), or serum potassium (K).

(27) The use according to any one of the above (23) to (26), wherein the animal is an animal after surgery for the treatment of a disease selected from a genital disease, a tumor, a urological disease, a bone disease, disc hernia, and a gastrointestinal tract disease.

(28) The use according to any one of the above (23) to (26), wherein the animal is an animal under medical treatment for a disease selected from lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, feline acquired immunodeficiency syndrome (FIV), feline leukemia virus (FELV) infection, canine parvovirus (CPV) infection, feline viral rhinotracheitis (FVR), a liver disease, filariasis, hemobartonellosis, babesiosis, habu bite, anaphylaxis, a falling accident, rib fracture, and burn.

(29) The use according to any one of the above (23) to (28), wherein a combination of a reason for medical treatment and an evaluation parameter is one of the following: 1) the reason for the medical treatment is pyometra or surgical removal of a reproductive organ, and the evaluation parameter is improvement of body temperature; 2) the reason for the medical treatment is mammary gland tumor, and the evaluation parameter is improvement of vigor; 3) the reason for the medical treatment is a fracture or an accident, and the evaluation parameter is improvement of vigor or improvement of GOT, GPT, and/or creatinine value, which are biochemical test values; 4) the reason for the medical treatment is urethral opening formation, and the evaluation parameter is improvement of platelet count and/or white blood cell count, which are blood cell test values, or improvement of creatinine value, which is a biochemical test value; 5) the reason for the medical treatment is stillbirth or dystocia, and the evaluation parameter is improvement of body temperature; 6) the reason for the medical treatment is an infection, and the evaluation parameter is improvement of vigor, stabilization of a high respiratory rate, or improvement of serum potassium value or GOT and/or GPT, which are a biochemical test value; 7) the reason for the medical treatment is renal dysfunction, and the evaluation parameter is vigor, improvement of white blood cell count, which is a blood cell test value, or improvement of ALP and/or CPK, which are biochemical test values; and 8) the reason for the medical treatment is anaphylaxis, and the evaluation parameter is vigor or serum ammonia value, which is a biochemical test value.
(30) The use according to any one of the above (23) to (29), wherein the ghrelin or a derivative thereof is a peptide, or a pharmaceutically acceptable salt thereof, selected from the group consisting of (i) a peptide which has any one of amino acid sequences of SEQ ID NOS: 1 to 23 in which the amino acid residue at the 3rd position from the amino terminus is a modified amino acid residue containing a fatty acid introduced into a side chain thereof and (ii) a peptide which has an amino acid sequence including deletion, substitution, and/or addition of one to several amino acids in an amino acid sequence between the amino acid residue at the 5th position and the amino acid residue at the 28th position from the amino terminus in any one of amino acid sequences of SEQ ID NOS: 1 to 23 in which the amino acid residue at the 3rd position from the amino terminus is a modified amino acid residue containing a fatty acid introduced into a side chain thereof, and has an action of increasing intracellular calcium concentration by acting on a GHS receptor.
(31) The use according to the above (30), wherein the ghrelin is a peptide that has an amino acid sequence of SEQ ID NO: 1 in which the serine residue at the 3rd position from the amino terminus is a modified amino acid residue containing a fatty acid introduced into a side chain hydroxyl group thereof.
(32) The use according to the above (31), wherein the ghrelin is a peptide that has an amino acid sequence of SEQ ID NO: 1 in which the side chain hydroxyl group of the serine residue at the 3rd position from the amino terminus is acylated with an n-octanoyl group.
(33) The use according to any one of the above (23) to (32), wherein the therapeutic agent for accelerating recovery contains 0.001 to 100 mg per dose unit of ghrelin or a derivative thereof as an active ingredient.

EXAMPLES

Hereafter, the present invention will be specifically described with reference to the following Examples.

In these Examples, a canine-derived ghrelin (a peptide compound in which a side chain hydroxyl group of the serine residue at the 3rd position from the amino terminus is acylated with an n-octanoyl group in SEQ ID NO: 1) was used as ghrelin. The canine-derived ghrelin was chemically synthesized and then lyophilized, and a canine-derived ghrelin for administration containing 0.1, 0.3, 0.5, or 1 mg per vial of a canine-derived ghrelin was prepared.

To administer ghrelin to animals, the canine-derived ghrelin was dissolved to a concentration of 1 mg/2 mL in physiological saline and intravenously, subcutaneously, or intramuscularly injected after the dose was adjusted depending on the body weight.

Of animals which had a decreased activity (vigor), were exhausted, and required medical treatment, animals for which the need to improve physical conditions thereof was recognized were used. Animals hospitalized in veterinary hospitals, particularly canines and felines, were used for treatment. These animals may or may not have undergone a surgery for treatment. The surgeries performed on the animals were pyometra surgery, surgical removal of a reproductive organ, surgical removal of mammary gland tumor, ovary cyst surgery, liver cell tumor surgery, disc hernia surgery, diaphragmatic hernia surgery, fracture surgery, gastrointestinal tract surgery, and urethroplasty.

Physical conditions in animals with various pathological conditions were examined by measuring parameters including activity (vigor), blood cell test values, biochemical test values, urinalysis, electrolyte tests, body weight, body temperature, the degree of anger or anxiety, respiratory rate, and the like to evaluate the effect of improving physical conditions in the animals. The effect was evaluated by comparing various evaluation parameters before and after administration.

The evaluation parameters used were activity (vigor), body temperature, hematology parameters (blood cell test values), serum biochemistry parameters (biochemical test values), the degree of anger or anxiety, and respiratory rate. To evaluate activity (vigor), physical conditions observed visually by an observer were evaluated using the following scores and criteria: 1. lifeless (the animal has lost vigor) (the animal is unable to move and exhausted), 2. slightly responsive to an external stimulus (the animal is slightly responsive to movement of a health care professional, follows with the eyes, lifts the head, or tries to get up), 3. capable of moving in response to an external stimulus (the animal is able to get up and move in the cage although slowly), 4. as usual with normal movement, 5. more active than normal, 6. considerably more active than normal, and 7. very active. The degree of anger or anxiety of an animal observed visually by an observer were also evaluated using the following criteria: 1. calm and accustomed to a health care professional, 2. able to be touched by but unaccustomed to a health care professional and restless, 3. wandering around or hiding in the kennel with anxiety, 4. able to be barely touched, and 5. too violent to be touched by a health care professional and tends to bite.

Example 1

Therapeutic Effect of Ghrelin (Single Dose) in Hospitalized Animals with Various Pathological Conditions after Surgery 13.2 to 80 μg/kg of a canine-derived ghrelin (chemically synthesized) was administered by an intravenous injection, a subcutaneous injection, or an intramuscular injection (solution for an injection: physiological saline or the like) to 32 animals (canines and felines) after surgery which were hospitalized in veterinary hospitals. The 32 cases of the animals were as follows.

Pyometra surgery and surgical removal of reproductive organ, 18 animals; mammary gland tumor surgery, three animals (including one animal also having pyometra); disc hernia surgery, two animals; surgery for a fracture or a traffic accident injury, three animals; urethroplasty, three animals; gastrointestinal tract surgery, two animals; and pneumothorax surgery, one animal.

Improvement of physical conditions of these animals was evaluated in terms of activity (vigor), body temperature, hematology parameters (blood cell test values), and serum biochemistry parameters (biochemical test values).

Results are shown in Table 1.

The effect of accelerating the improvement of physical conditions in animals was observed in the animals which had underwent the surgeries shown below. The figures in parentheses with the evaluation parameters represent the number of animals which showed an improvement effect/the number of animals evaluated (response rate).

The response rate for improvement inactivity (vigor) was 91.7% (11/12). The response rate by surgery was 85.7% (6/7) in animals after pyometra surgery and surgical removal of a reproductive organ, 100% (2/2) in animals after surgical removal of mammary gland tumor, 100% (3/3) in animals after surgery for a fracture and an injury from a traffic accident, and 100% (1/1) in animals after urethroplasty. In particular, recovery of the animals which could not get up before administration of ghrelin was unpredictably favorable and remarkable.

The response rate for improvement of hyperthermia was 62.5% (5/8). The response rate by surgery was 75% (3/4) in animals after a pyometra surgery and surgical removal of a reproductive organ, 100% (1/1) in an animal after a mammary gland tumor surgery, 100% (1/1) in an animal after disc herniation surgery, and 100% (1/1) in an animal after a gastrointestinal tract surgery.

The response rate for the improvement of hematology parameters (blood cell test values) was 66.7% (4/6). The response rate by surgery was 75% (3/4) in animals after a pyometra surgery and surgical removal of a reproductive organ, 100% (1/1) in an animal after a mammary gland tumor surgery, and 50% (1/2) in animals after urethroplasty. For example, high white blood cell count was decreased ($44.1 \times 10^3/\mu L \rightarrow 17.7 \times 10^3/\mu L$), low red blood cell count was increased ($214 \times 10^4/\mu L \rightarrow 304 \times 10^4/\mu L$), low platelet count was increased ($13.9 \times 10^4/\mu L \rightarrow 58.5 \times 10^4/\mu L$), and low hemoglobin level was increased (5.1 mg/dL→7.7 mg/dL).

The response rate for the improvement of serum biochemistry parameters (biochemical test values) was 85.7% (6/7). The response rate by surgery was 100% (3/3) in animals after a pyometra surgery and surgical removal of a reproductive organ, 100% (1/1) in an animal after a mammary gland tumor surgery, 50% (1/2) in animals after urethroplasty, and 100% (1/1) in an animal after a gastrointestinal tract surgery. For example, high glutamic pyruvic transaminase (GPT) value was decreased (180 IU/L→85 IU/L), high total cholesterol (T-CHO) value was decreased (405 mg/dL→260 mg/dL), high alkaline phosphatase (ALP) value was decreased (345 IU/L→286 IU/L), high blood urea nitrogen (BUN) value was decreased (44.2 mg/dL→29.3 mg/dL), high serum creatinine (Cre) value was decreased (6.0 mg/dL→1.1 mg/dL), high creatinine phosphokinase (CPK) value was decreased (1429 IU/L→955 IU/L), and C-reactive protein (CRP) value was decreased upper limit of measurement →7.3 mg/dL).

TABLE 1

Evaluation of parameters indicating improvement of physical conditions in animals after administration of ghrelin after surgery

|  | Activity (vigor) | Body temperature | Hematology tests | Biochemical tests |
|---|---|---|---|---|
| Pyometra surgery and surgical removal of reproductive organ: 18 animals | 6/7 (85.7%) | 3/4 (75.0%) | 3/4 (75.0%) | 3/3 (100%) |
| Surgical removal of mammary gland tumor: 3 animals* | 2/2 (100%) | 1/1 (100%) | 1/1 (100%) | 1/1 (100%) |
| Surgery for fracture or traffic accident injury: 3 animals | 3/3 (100%) | — | — | — |
| Urethroplasty: 3 animals | 1/1 (100%) | 0/1 (0%) | 1/2 (50.0%) | 1/2 (50.0%) |
| Disc hernia surgery: 2 animals | — | 1/1 (100%) | — | — |
| Gastrointestinal tract surgery: 2 animals | — | 1/1 (100%) | — | 1/1 (100%) |
| Pneumothorax surgery: 1 animal | — | 0/1 (0%) | — | — |
| Total: 32 animals | 11/12 (91.7%) | 5/8 (62.5%) | 4/6 (66.7%) | 5/6 (83.3%) |

*Since one animal which had pyometra concurrently is included in the animals with mammary gland tumor, the total number does not match the sum of all columns.

From the above results, when ghrelin was administered to animals after surgery for the treatment of diseases showing the above symptoms or of the above symptoms, the parameters indicating physical conditions in animals with specific diseases or symptoms were improved, and a return from physical conditions of decreased activity (vigor) and exhaustion to normal was accelerated in animals under medical treatment.

Example 2

Therapeutic Effect of Ghrelin (Single Dose) in Animals Under Medical Treatment which Had Physical Conditions Worsen by Various Diseases Since administration of ghrelin improved activity (vigor), hyperthermia, hematology parameters (white blood cell and platelet) and biochemistry parameters (GPT, BUN, etc.) in animals after surgery, improvement of these parameters after administration of ghrelin was expected to be associated with acceleration of a return to normal physical conditions of animals with other diseases.

Accordingly, 12.9 to 67.9 µg/kg of ghrelin was administered by an intravenous injection, a subcutaneous injection, or an intramuscular injection to animals which had a decreased activity (vigor) and was exhausted, for example, 18 animals under medical treatment for pathological conditions other than a surgery to evaluate the improvement of physical conditions in animals worsened by pathological conditions other than surgery in terms of activity (vigor), hematology parameters (blood cell test values), biochemistry parameters (biochemical test values), body temperature, and the like.

Ten animals had two or more diseases concurrently. The diseases including concurrent diseases were as follows: lower urological syndrome, urinary retention, infectious respiratory syndrome, chronic renal failure, osteoarthritis, chronic hepatitis, cystolithiasis, malnutrition, debility, jaundice, circulatory insufficiency, multiple organ failure, pulmonary edema, anemia, tabefaction, diarrhea, vomiting, wheezing, pyrexia, FIV, FELV infection, CPV infection, FVR, a liver disease, filariasis, hemobartonellosis, babesiosis, habu bite, anaphylaxis, a falling accident, rib fracture, and burn.

Of the animals with these diseases, the evaluation parameters recorded in medical records were as follows: activity (vigor) in 16 animals, biochemistry parameters (biochemical test values) in 11 animals, hematology parameters (blood cell test values) in three animals, and body temperature in one animal.

After administration of ghrelin, activity (vigor) was improved in 16/16 animals (for example, unable to move [a score of 1]→capable of moving in response to an external stimulus [a score of 3]). Body temperature was improved in 1/1 animal (for example, 40.2° C.→37.8° C.). Hematology parameters (blood cell test values) (the white blood cell count [for example, $278 \times 10^2/\mu L \rightarrow 167 \times 10^2/\mu L$] and the platelet count [for example, $10 \times 10^5/\mu L \rightarrow 26.9 \times 10^5/\mu L$]) were improved in 3/3 animals. Biochemistry parameters (biochemical test values) (GPT [for example, 670 IU/L→260 IU/L], GOT [for example, >1000 IU/L→187 IU/L], CPK [for example, 1166 IU/L→64 IU/L], ALP [for example, 643 IU/L→291 IU/L], BUN [for example, 72.5 mg/dL→15.4 mg/dL], Cre [for example, 3.2 mg/dL→1.3 mg/dL], $NH_3$ [for example, 207 µg/dL→302 µg/dL], T-bil [18.8 mg/dL→4.9 mg/dL]) were improved in 11/11 animals. Results are shown in Table 2.

As described above, the improvement of these parameters observed after administration of ghrelin in the animals with poor physical conditions after surgery was similarly observed in the animals with poor physical conditions other than pathological conditions worsened by a surgery.

In other words, administration of ghrelin was found to be useful for accelerating the recovery of animals which had a decreased activity (vigor) and was exhausted, for example, animals with poor physical conditions after surgery and animals with poor physical conditions due to diseases.

TABLE 2

Evaluation of parameters indicating improvement of physical conditions in animals under medical treatment for various diseases after administration of ghrelin

|  | Activity (vigor) | Body temperature | Hematology tests | Biochemical tests |
|---|---|---|---|---|
| Infection: 8 animals | 6/6 (100%) | — | 1/1 (100%) | 6/6 (100%) |
| Renal dysfunction: 3 animals | 3/3 (100%) | — | 2/2 (100%) | 1/1 (100%) |
| Accident etc.: 3 animals | 3/3 (100%) | — | — | 1/1 (100%) |
| Liver disease: 1 animal | 1/1 (100%) | 1/1 (100%) | — | — |
| Debility: 1 animal | 1/1 (100%) | — | — | 1/1 (100%) |
| Anaphylaxis: 1 animal | 1/1 (100%) | — | — | 1/1 (100%) |
| Multiple organ failure: 1 animal | 1/1 (100%) | — | — | — |
| Total: 18 animals | 16/16 (100%) | 1/1 (100%) | 3/3 (100%) | 11/11 (100%) |

Details of pathological conditions listed in Table 2 are as follows.
Infection (FIV, FELV infection, CPV infection, FVR, filariasis, hemobartonellosis, and babesiosis)
Renal dysfunction (lower urological syndrome, urinary retention, chronic renal failure, and cystolithiasis)
Accident etc. (falling accident, rib fracture, and burn)

Example 3

3-1. Improvement of Physical Conditions in Animals Under Medical Treatment after Administration of Ghrelin in Various Disease Groups Repeated Dose As animals which had a decreased activity (vigor) and were exhausted, animals (a total of 48 canines and felines combined) which were hospitalized in veterinary hospitals and had poor physical conditions due to a surgery, a chronic or acute disease, or the like were used. A canine-derived ghrelin was repeatedly administered intravenously or subcutaneously to each of the animals with poor physical conditions. The dose of intravenous administration was approximately 5 µg/kg or 10 µg/kg, and the dose of subcutaneous administration was approximately 100 µg/kg. The mean number of doses in repeated administration was approximately four times, and the maximum number of doses was 11 times. The administration period was one to six days.

Evaluation parameters evaluated before and after administration of ghrelin were appetite, quantity of meal, biochemical test values (GOT, GPT, BUN, CRE, CPK, CRP), blood cell test values (white blood cell [WBC], platelet [PLT]), body temperature, activity (vigor), skin, coat, wellness, the degree of anger or anxiety, respiratory rate, and others. These parameters were analyzed together with the results of the animals receiving a single dose (Examples 1 and 2). The analysis results were compiled by disease, such as renal dysfunction, tumor, fracture, and accident (see Table 3-1). Statistical analysis of values before and after administration was performed using a paired t-test. If there were two or less pairs of corresponding values before and after administration, and two or more values did not have corresponding values, the analysis was performed using an unpaired t-test.

Result 1. Renal Dysfunctions (10 Animals)

Ghrelin was administered to hospitalized animals under medical treatment which were confirmed to have a renal dysfunction, such as chronic renal failure, renal failure, urinary retention, urolithiasis, or cystolithiasis, and had poor physical conditions. The analysis of parameters before and after administration of ghrelin showed improvement in the white blood cell (WBC) count (5/5 animals, $324 \times 10^2/\mu L \rightarrow 139 \times 10^2/\mu L$) and the platelet (PLT) count (4/5 animals, $11.3 \times 10^5/\mu L \rightarrow 23.6 \times 10^5/\mu L$), which are hematology parameters, the serum creatinine (CRE) value (3/3 animals, 3.2 mg/dL→1.3 mg/dL), which is a serum biochemistry parameter, and the score of activity (vigor) (5/6 animals) (for example, a score of 2 [slightly responsive to an external stimulus]→a score of 3 [capable of moving in response to an external stimulus]). Administration of ghrelin to animals with a renal dysfunction was found to accelerate a return of poor physical conditions to normal. Specifically, administration of ghrelin decreased the white blood cell count increased while an inflammation occurred, increased the decreased platelet count, which indicates a state of the coagulation and fibrinolytic system, decreased the increased creatinine, which is an indicator of renal function, and improved activity (vigor), which indicates vitality of animals.

Result 2. Tumors (14 Animals)

Ghrelin was administered to animals which were confirmed to have mammary gland tumor, salivary gland tumor, tongue tumor, tongue angiosarcoma, adenoma in the perianal region, or tumor (tumor mass) such as subcutaneous tumor mass, liver tumor mass, and testicle mass and had poor physical conditions. The analysis of parameters before and after administration of ghrelin showed improvement in activity (vigor) (7/8 animals) (for example, a score of 3 [capable of moving in response to an external stimulus]→a score of 6 [considerably more active than normal]), body temperature (6/6 animals, 39.8° C.→38.6° C.), and the degree of anger or anxiety (4/6 animals) (for example, a score of 5 [too violent to be touched and tends to bite]→a score of 2 [able to be touched by but unaccustomed to a health care professional]). Administration of ghrelin to animals with a tumor (tumor mass) accelerated a return of the poor physical conditions in animals to normal. Specifically, administration of ghrelin improved the activity (vigor), decreased the body temperature increased by an inflammation or the like, and decreased the degree of anger or anxiety, which are indicators of excitation and anxiety in animals.

Result 3. Fractures, Accidents, Etc. (Nine Animals)

Ghrelin was administered to animals under medical treatment for a fracture resulting from a traffic accident or a falling accident, trauma, luxation, disc hernia, or bone resorption and had poor physical conditions. The analysis of parameters before and after administration of ghrelin showed improvement in the serum biochemistry parameters, i.e., the glutamic oxaloacetic transaminase (GOT) value, which is an indicator of disorders of the organs such as the liver, the heart, the kidneys, and muscles (6/6 animals, 996 IU/L→22 IU/L), the glutamic pyruvic transaminase (GPT) value, which is primarily an indicator of hepatopathy (6/7 animals, 1000 IU/L→32 IU/L), the blood urea nitrogen (BUN) value, which is an indicator of renal dysfunction (6/7 animals, 18.3 mg/dL→10.6 mg/dL), and the creatine phosphokinase (CPK) value, which is an indicator of injury of a cardiac muscle or skeletal muscle (2/2 animals, 42.4 IU/L→9.4 IU/L), the activity (vigor) (13/16 animals) {for example, a score of 1 (unable to move [cannot stand up])→a score of 3 (capable of moving in response to an external stimulus [able to get up])}, the body temperature (5/7 animals, 39.2° C.→38.0° C.), the degree of anger or anxiety (6/10 animals) (for example, a score of 5 [too violent to be touched and tends to bite]→a score of 1 [calm]), and the increased respiratory rate diagnosed as high respiratory rate, voluntary ventilation, or the like (2/2 animals, 100/min→50/min). These results demonstrated that administration of ghrelin to animals with poor physical conditions due to a fracture, an accident, or the like improved the GOT value, the GPT value, the CPK value, the activity (vigor), the body temperature, the degree of anger or anxiety, and the respiratory rate and accelerated a return of poor physical conditions due to a fracture, an accident, or the like to normal.

Result 4. Genital Diseases (29 Animals)

Ghrelin was administered to animals whose reproductive organ was removed for pyometra, contraception, or castration and which had poor physical conditions. The analysis of parameters before and after administration of ghrelin showed improvement in the BUN value (3/3 animals, 31.5 mg/dL→7.1 mg/dL) and the CRP value (5/5 animals, 100 mg/dL→16 mg/dL), which are serum biochemistry parameters (biochemical test values), the activity (vigor) (13/15 animals) {for example, a score of 1 (lifeless)→a score of 3 (capable of moving in response to an external stimulus [able to get up])}, and the body temperature (11/11 animals, 40.1° C.→38.1° C.). These results demonstrated that administration of ghrelin to animals with poor physical conditions due to surgical removal of a reproductive organ improved the high BUN value, decreased the CRP value increased by an inflammation, improved the activity (vigor), which indicates vitality of animals, improved the body temperature increased by an inflammation, and accelerated a return of poor physical condition due to surgical removal of a reproductive organ to normal.

Result 5. Infections and Parasitism (15 Animals)

Ghrelin was administered to animals which were under medical treatment for an infection or a parasitism, such as FIV, FELV infection, CPV infection, FVR, infectious respiratory syndrome, babesiosis, hemobartonellosis, and filariasis and had poor physical conditions. The analysis of parameters before and after administration of ghrelin showed improvement in the BUN value (2/2 animals, 23.4 mg/dL→16.4 mg/dL), which is a serum biochemistry parameter (biochemical test value), and the activity (vigor) (10/11 animals) {for example, a score of 1 (lifeless)→a score of 3 (capable of moving in response to an external stimulus [able to get up])}, and the respiratory rate (3/3 animals, 100/min→70/min). These results demonstrated that administration of ghrelin to animals with poor physical conditions due to an infection or a parasitism improved the high BUN value, improved the activity (vigor), which indicates vitality of animals, improve the increased respiratory rate due to a decreased oxygen exchanging ability, and accelerated a return of poor physical conditions due to an infection or a parasitism to normal.

Result 6. Inflammatory Diseases (13 Animals)

Ghrelin was administered to animals which were under medical treatment for dermatitis, multiple organ failure, bite, cleft palate injury, buttock trauma, or the like and had poor physical condition. The analysis of parameters before and after administration of ghrelin showed improvement in the GOT value (3/4 animals, 149 IU/L→25.0 IU/L), the GPT value (4/4 animals, 1000 IU/L→282 IU/L), and the BUN value (4/4 animals, 18.6 mg/dL→10.7 mg/dL), which are serum biochemistry parameters (biochemical test values), the eters before and after administration of ghrelin showed improvement in the activity (vigor) (5/5 animals) {for example, a score of 1 (unable to move [unable to walk])→a score of 5 (more active than normal)}. These results demonstrated that administration of ghrelin to animals with poor physical condition due to various gastrointestinal tract diseases improved the activity (vigor).

TABLE 3-1

Evaluation of improvement of parameters indicating physical conditions in animals under medical treatment for various diseases after administration of ghrelin

| Disease | No. of animals | WBC | PLT | GOT | GPT | BUN | CRE |
|---|---|---|---|---|---|---|---|
| Renal dysfunction | 10 | 5/5 Decreased* | 4/5 Increased** | 0/1 | 1/1 | 2/3 | 3/3 Decreased* |
| Tumor | 14 | 3/6 | 3/6 | 3/5 | 4/6 | 2/4 | 2/4 |
| Fracture, accident, etc. | 19 | 3/7 | 4/8 | 6/6 Decreased* | 6/7 Decreased* | 6/7 Decreased* | 2/3 |
| Genital disease | 29 | 5/7 | 4/7 | 3/3 | 4/4 | 3/3 Decreased* | 1/2 |
| Infection or parasitism | 15 | 1/4 | 3/4 | 1/2 | 3/4 | 2/2 Decreased* | 1/1 |
| Gastrointestinal tract disease | 7 | 2/2 | 0/1 | 3/3 | 3/3 | 1/1 | — |
| Inflammatory disease | 13 | 3/4 | 2/4 | 3/4 Decreased* | 4/4 Decreased* | 4/4 Decreased* | 0/2 |

| Disease | CPK | CRP | Vigor | Body temperature | Degree of anger | Respiratory rate |
|---|---|---|---|---|---|---|
| Renal dysfunction | — | — | 5/6 Improved** | 2/2 | 1/3 | 1/1 |
| Tumor | — | 2/2 | 7/8 Improved* | 6/6 Decreased* | 4/6 Improved* | 1/1 |
| Fracture, accident, etc. | 2/2 Decreased* | — | 13/16 Improved** | 5/7 Decreased* | 6/10 Improved* | 2/2# |
| Genital disease | — | 5/5 Decreased* | 13/15 Improved** | 11/11 Decreased** | 2/8 | 1/1 |
| Infection or parasitism | 1/1 | — | 10/11 Improved** | 3/3 | 0/2 | 3/3 Improved* |
| Gastrointestinal tract disease | 2/2 | — | 5/5 Improved* | 2/3 | 0/1 | 1/ |
| Inflammatory disease | 1/1 | 1/2 | 9/9 Improved* | 5/6 Decreased* | 2/5 | 2/2# |

*p < 0.05
**p < 0.01
The respiratory rate was stabilized in 2 of 2 animals.
Note:
The t-test did not show a statistical significance in parameters without asterisks although 3/3 etc. is indicated.
Abbreviations:
WBC, white blood cell;
PLT, platelet;
GOT, glutamic oxaloacetic transaminase;
GPT, glutamic pyruvic transaminase;
BUN, blood urea nitrogen;
CRE, creatinine;
CPK, creatinine phosphokinase;
CRP, C-reactive protein.

activity (vigor) (9/9 animals) {for example, a score of 1 (exhausted)→a score of 3 (capable of moving in response to an external stimulus [able to get up])}, and the body temperature (5/6 animals, 39.8° C.→38.7° C.). These results demonstrated that administration of ghrelin to animals with poor physical condition due to various inflammatory diseases improved the GOT value, the GPT value, the BUN value, body temperature, and the activity (vigor).

Result 7. Gastrointestinal Tract Diseases (7 Animals)

Ghrelin was administered to animals which were under medical treatment for vomiting, diarrhea, multiple organ failure, intussusception, gastric volvulus, acute enteritis, or the like and had poor physical conditions. The analysis of param- 3-2. Improvement of Physical Conditions after Administration of Ghrelin in Animals which Had Undergone a Surgery or Had not Undergone a Surgery Ghrelin was administered to animals with poor physical conditions after surgery for the treatment of various pathological conditions, and various parameters indicating physical conditions before and after administration of ghrelin were analyzed. The surgery included urethroplasty, surgery for a fracture, luxation, disc hernia, or diaphragmatic hernia, surgical removal of a tumor, and surgical removal of a reproductive organ due to pyometra. The results showed improvement in the activity (vigor), the platelet (PLT) count, which is a hematology test value, the GOT value, the GPT value, the BUN value, and the CRE value, which are biochemical test values, the body temperature, the degree of anger or anxiety, and the respiratory rate (see Table 3-2).

Meanwhile, ghrelin was administered to animals with poor physical conditions due to various pathological conditions which had not undergone a surgery, and various parameters indicating physical conditions before and after administration of ghrelin were analyzed. The pathological conditions included filariasis, mite infestation, babesiosis, hemobartonellosis, bite, and dermatitis. The results showed improvement in the activity (vigor), the white blood cell (WBC) count, which is a blood cell test value, the GPT value and the BUN value, which are biochemical test values (see Table 3-2).

From the above, administration of ghrelin to animals with poor physical conditions and under medical treatment, whether or not the animals had undergone a surgery, accelerated a return of physical conditions of the animals to normal. Furthermore, parameters showing a significant difference in the animals after surgery were compared with parameters showing a significant difference in the animals which had not undergone a surgery. The results showed that more parameters provided a significant difference in animals after surgery than in animals which had not undergone a surgery. The results indicates that administration of a canine-derived ghrelin to animals which have a decreased activity (vigor), are exhausted, and are under medical treatment produces a particularly marked effect in animals after surgery.

TABLE 3-2

Improvement of physical conditions after administration of canine-derived ghrelin to animals which had undergone a surgery or had not undergone a surgery

| Treatment | No. of animals | WBC | PLT | GOT | GPT | BUN | CRE | Vigor | Body temperature | Degree of anger | Respiratory rate |
|---|---|---|---|---|---|---|---|---|---|---|---|
| Surgery | 70 | — | $p < 0.05$ | $p < 0.01$ | $p < 0.01$ | $p < 0.05$ | $p < 0.05$ | $p < 0.01$ | $p < 0.01$ | $p < 0.01$ | $p < 0.05$ |
| No surgery | 24 | $p < 0.05$ | — | — | $p < 0.05$ | $p < 0.05$ | — | $p < 0.01$ | — | — | — |

Example 4

Improvement of Physical Conditions in Animals which Did not Ingest Food after Administration of Ghrelin Diseases: Rib fracture, chronic renal failure, falling accident, infectious respiratory syndrome, hemobartonellosis, FIV, FELV infection, CPV infection, habu bite, diarrhea, vomiting, mammary gland tumor, traffic accident, fracture surgery, urinary retention, renal failure, urethroplasty, urinary retention, forelimb trauma Number of animals: 15
Activity improved: 11/13 (2, not evaluated; 2 unchanged)
GPT value improved: 3/3
GOT value improved: 2/2
BUN value improved: 2/2
CRE value improved: 2/2
CPK value improved: 1/1
ALP value improved: 1/1
WBC value improved: 1/1 (decreased)
PLT value improved: 2/2
Body temperature decreased: 2/2

Of the animals analyzed in Example 3, animals which did not ingest food after administration of ghrelin were analyzed for improvement in evaluation parameters of activity (vigor), blood cell test values, biochemical test values, the degree of anger or anxiety, body temperature, and respiratory rate.

The results of Example 4 showed improvement in one or more of activity (vigor), blood cell test values, biochemical test values, and body temperature in animals which did not ingest food after administration of ghrelin. This indicates that these parameters were improved not by food ingestion but by ghrelin.

INDUSTRIAL APPLICABILITY

The present invention is useful for the medical and veterinary fields.

The invention claimed is:

1. A treatment method for accelerating the improvement of a physical condition in a canine or a feline under medical treatment which has a decreased activity (vigor), comprising administration of ghrelin or a derivative thereof or a pharmaceutically acceptable salt thereof to the canine or the feline under medical treatment to improve one or more evaluation parameters selected from the group consisting of: activity (vigor), blood cell test values, biochemical test values, body temperature, degree of anger or anxiety, and respiratory rate, wherein the reason for the medical treatment is chronic renal failure and the condition of the canine or the feline under medical treatment is, in terms of activity (vigor), Score 1: lifeless (loss of vigor) (unable to move) or Score 2: slightly responsive to an external stimulus (slightly responsive to the movement of a health care professional, follows with the eyes, lifts the head, or tries to get up).

2. The treatment method according to claim 1, which improves one or more evaluation parameters selected from the group consisting of: activity (vigor), blood cell test values, biochemical test values, and body temperature, without ingesting food after administering ghrelin.

3. The treatment method according to claim 1, which improves at least activity (vigor).

4. The treatment method according to claim 3, wherein the evaluation parameter to be improved is, in addition to the canine's or the feline's ability to move, at least one of body temperature, the blood cell test values, and the biochemical test values.

5. The treatment method according to claim 1, wherein the improvement of activity (vigor) is that a canine or a feline unable to move becomes able to move.

6. The treatment method according to claim 1, wherein the canine or the feline has undergone surgery.

7. The treatment method according to claim 1, wherein the blood cell in the blood cell test values is white blood cell, platelet, or hemoglobin.

8. The treatment method according to claim 1, wherein the biochemical test value is at least one selected from the group consisting of the values of glutamic pyruvic transaminase (GPT), glutamic oxaloacetic transaminase (GOT), total cholesterol (T-CHO), alkaline phosphatase (ALP), blood urea nitrogen (BUN), serum creatinine (CRE), blood ammonia ($NH_3$), total bilirubin (T-bil), creatinine phosphokinase (CPK), serum potassium (K), C-reactive protein (CRP), LDH, γ-GTP, CHE, and CK.

9. The treatment method according to claim 1, wherein the biochemical test value is at least one selected from the group consisting of the values of GOT, GPT, LDH, ALP, γ-GTP, CHE, CK, bilirubin, and CRE, as biochemical test values unaffected by meal.

10. The treatment method according to claim 1, comprising administration of ghrelin or a derivative thereof or a pharmaceutically acceptable salt thereof to the canine or the feline to improve the activity (vigor) of the canine or the feline so that the canine or the feline unable to move becomes able to move and to improve one or more evaluation parameters selected from the group consisting of: blood cell test values, biochemical test values, body temperature, and degree of anger or anxiety.

11. The treatment method according to claim 10, wherein the condition of the canine or the feline under medical treatment satisfies one or more evaluation parameters selected from the group consisting of: a biochemical test value GOT is 996 IU/L or higher, a biochemical test value GPT is 1000 IU/L or higher, a biochemical test value BUN is 18.3 mg/dL or higher, and body temperature is 39.2° C. or higher.

12. The treatment method according to claim 10, wherein the ghrelin or a derivative thereof or a pharmaceutically acceptable salt thereof is administered intravenously or subcutaneously one to several times per day for 1 to 6 days.

13. The treatment method according to claim 1, comprising administration of ghrelin or a derivative thereof or a pharmaceutically acceptable salt thereof to the canine or the feline to improve degree of anger or anxiety of the canine or the feline and to improve one or more evaluation parameters selected from the group consisting of activity (vigor), blood cell test values, biochemical test values, body temperature, and respiratory rate.

14. The treatment method according to claim 13, wherein the ghrelin or a derivative thereof or a pharmaceutically acceptable salt thereof is administered intravenously or subcutaneously one to several times per day for 1 to 6 days.

15. The treatment method according to claim 1, comprising administration of ghrelin or a derivative thereof or a pharmaceutically acceptable salt thereof to the canine or the feline to improve one or more evaluation parameters selected from the group consisting of: activity (vigor), blood cell test values, GOT, GPT, and BUN, which are biochemical test values, degree of anger or anxiety, body temperature, and respiratory rate.

16. The treatment method according to claim 15, wherein the condition of the canine or the feline under medical treatment satisfies one or more evaluation parameters selected from the group consisting of: platelet count, which is a blood cell test value, is $11.3 \times 10^5/\mu L$ or lower; a biochemical test value GOT is 996 IU/L or higher; a biochemical test value GPT is 1000 IU/L or higher; a biochemical test value BUN is 23.4 to 44.2 mg/dL; body temperature is 39.2 to 40.1° C.; and respiratory rate is 100 breaths/minute or more.

17. The treatment method according to claim 15, wherein the ghrelin or a derivative thereof or a pharmaceutically acceptable salt thereof is administered intravenously or subcutaneously one to several times per day for 1 to 6 days.

18. A method for accelerating the improvement of a physical condition in a canine or a feline under medical treatment which has a decreased activity (vigor), comprising administration of ghrelin or a derivative thereof or a pharmaceutically acceptable salt thereof to the canine or the feline to improve the activity (vigor) of the canine or the feline so that the canine or the feline unable to move becomes able to move, and to improve one or more evaluation parameters selected from the group consisting of: blood cell test values, biochemical test values, body temperature, and degree of anger or anxiety, wherein the reason for the medical treatment is chronic renal failure and the condition of the canine or the feline under medical treatment is, in terms of activity (vigor), Score 1: lifeless (loss of vigor) (unable to move) or Score 2: slightly responsive to an external stimulus (slightly responsive to the movement of a health care professional, follows with the eyes, lilts the head, or tries to get up).

19. The method according to claim 18, wherein the condition of the canine or the feline under medical treatment satisfies one or more evaluation parameters selected from the group consisting of: a biochemical test value GOT is 996 IU/L or higher, a biochemical test value GPT is 1000 IU/L or higher, a biochemical test value BUN is 18.3 mg/dL or higher, and body temperature is 39.2° C. or higher.

20. The method according to claim 18, wherein the ghrelin or a derivative thereof or a pharmaceutically acceptable salt thereof is administered intravenously or subcutaneously one to several times per day for 1 to 6 days.

21. A method for accelerating the improvement of a physical condition in a canine or a feline under medical treatment which has a decreased activity (vigor), comprising administration of ghrelin or a derivative thereof or a pharmaceutically acceptable salt thereof to the canine or the feline to improve degree of anger or anxiety of the canine or the feline and to improve one or more evaluation parameters selected from the group consisting of: activity (vigor), blood cell test values, biochemical test values, body temperature, and respiratory rate, wherein the reason for the medical treatment is chronic renal failure and the condition of the canine or the feline under medical treatment is, in terms of activity (vigor), Score 1: lifeless (loss of vigor) (unable to move) or Score 2: slightly responsive to an external stimulus (slightly responsive to the movement of a health care professional, follows with the eyes, lifts the head, or tries to get up).

22. The method according to claim 21, wherein the ghrelin or a derivative thereof or a pharmaceutically acceptable salt thereof is administered intravenously or subcutaneously one to several times per day for 1 to 6 days.

23. A method for accelerating the improvement of a physical condition in a canine or a feline under medical treatment which has a decreased activity (vigor), comprising administration of ghrelin or a derivative thereof or a pharmaceutically acceptable salt thereof to the canine or the feline to improve one or more evaluation parameters selected from the group consisting of: activity (vigor), blood cell test values, GOT, GPT, and BUN, which are biochemical test values, degree of anger or anxiety, body temperature, and respiratory rate, wherein the reason for the medical treatment is chronic renal failure and the condition of the canine or the feline under medical treatment is, in terms of activity (vigor), Score 1: lifeless (loss of vigor) (unable to move) or Score 2: slightly responsive to an external stimulus (slightly responsive to the movement of a health care professional, follows with the eyes, lifts the head, or tries to get up).

24. The method according to claim 23, wherein the condition of the canine or the feline under medical treatment satisfies one or more evaluation parameters selected from the group consisting of: platelet count, which is a blood cell test value, is $11.3 \times 10^5/\mu L$ or lower; a biochemical test value GOT is 996 IU/L or higher; a biochemical test value GPT is 1000 IU/L or higher; a biochemical test value BUN is 23.4 to 44.2 mg/dL; body temperature is 39.2 to 40.1° C.; and respiratory rate is 100 breaths/minute or more.

25. The method according to claim 23, wherein the ghrelin or a derivative thereof or a pharmaceutically acceptable salt thereof is administered intravenously or subcutaneously one to several times per day for 1 to 6 days.

\* \* \* \* \*